US012807994B2

(12) United States Patent
Gibbons

(10) Patent No.: US 12,807,994 B2
(45) Date of Patent: Nov. 24, 2026

(54) COMPOSITIONS AND METHODS FOR ANALYZING GENOMIC INSERTION SITES OF EXOGENOUS NUCLEIC ACIDS

(71) Applicant: 10x Genomics, Inc., Pleasanton, CA (US)

(72) Inventor: Michael Gibbons, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 19/114,574

(22) PCT Filed: Oct. 2, 2023

(86) PCT No.: PCT/US2023/075707

§ 371 (c)(1),
(2) Date: Mar. 24, 2025

(87) PCT Pub. No.: WO2024/076908

PCT Pub. Date: Apr. 11, 2024

(65) Prior Publication Data

US 2025/0257399 A1 Aug. 14, 2025

Related U.S. Application Data

(60) Provisional application No. 63/378,110, filed on Oct. 3, 2022.

(51) Int. Cl.
*C12Q 1/6876* (2018.01)
*C12Q 1/6874* (2018.01)

(52) U.S. Cl.
CPC ......... *C12Q 1/6876* (2013.01); *C12Q 1/6874* (2013.01); *C12Q 2600/16* (2013.01)

(58) Field of Classification Search
CPC ................ C12Q 1/6876; C12Q 1/6874; C12Q 2600/16; C12Q 1/6806; C12Q 1/6853
See application file for complete search history.

(56) References Cited

U.S. PATENT DOCUMENTS

| | | | |
|---|---|---|---|
| 2018/0105808 A1 | 4/2018 | Mikkelsen et al. | |
| 2019/0177800 A1 | 6/2019 | Boutet et al. | |
| 2019/0323088 A1 | 10/2019 | Boutet et al. | |
| 2019/0330694 A1 | 10/2019 | Schnall-Levin | |
| 2019/0361010 A1* | 11/2019 | Belhocine | G01N 33/54306 |
| 2019/0367969 A1 | 12/2019 | Belhocine et al. | |

FOREIGN PATENT DOCUMENTS

| | | |
|---|---|---|
| WO | 2018075693 A1 | 4/2018 |
| WO | 2018138237 A1 | 8/2018 |
| WO | 2019126789 A1 | 6/2019 |
| WO | 2019165318 A1 | 8/2019 |

OTHER PUBLICATIONS

Heaton et al., "souporcell: Robust clustering of single cell RNAseq by genotype without reference genotypes," Nature Methods 17(6):615-620, Jun. 1, 2020 (Europe PMC Funders Group Author Manuscript, available in PMC Dec. 9, 2024). (21 pages).

Huang et al., "Vireo: Bayesian demultiplexing of pooled single-cell RNA-seq data without genotype reference," Genome Biology 20:273, Dec. 13, 2019. (12 pages).

Hughes et al., "Choose Your Label Wisely: Water-Soluble Fluorophores Often Interact with Lipid Bilayers," PLoS ONE 9(2):e87649, Feb. 4, 2014. (8 pages).

Rosenberg et al., "SPLiT-seq reveals cell types and lineages in the developing brain and spinal cord," Science 360 (6385):176-182, Apr. 13, 2018 (HHS Public Access Author Manuscript, available in PMC Nov. 5, 2020). (16 pages).

Xu et al., "Genotype-free demultiplexing of pooled single-cell RNA-seq," Genome Biology 20:290, Dec. 19, 2019. (12 pages).

Wang et al., "Joint profiling of chromatin accessibility and CAR-T integration site analysis at population and single-cell levels," PNAS 117(10):5442-5452, Mar. 10, 2020 [Published online Feb. 24, 2020]. (11 pages).

* cited by examiner

*Primary Examiner* — Cynthia B Wilder

(74) *Attorney, Agent, or Firm* — Saul Ewing LLP; Justin W. Crotty; Thomas Murray

(57) ABSTRACT

The present disclosure relates generally to compositions, methods and systems for characterizing a biological particle, cell or cell nucleus, modified to include an exogenous insert, e.g., exogenous nucleic acids. The characterization may identify the insertion site of the exogenous nucleic acids in the biological particle's endogenous, e.g., genomic, nucleic acid sequences. Such characterization may be useful in the development of safer, more effective, modified cell biotherapeutics, e.g., cells modified to express chimeric antigen receptors.

34 Claims, 19 Drawing Sheets

COMPOSITIONS AND METHODS FOR ANALYZING GENOMIC INSERTION SITES OF EXOGENOUS NUCLEIC ACIDS

CROSS-REFERENCE TO RELATED APPLICATIONS

This application is a 35 U.S.C. § 371 national phase application of PCT International Patent Application No. PCT/US23/75707, filed Oct. 2, 2023, which claims the benefit of and priority to U.S. Provisional Patent Application No. 63/378,110, filed Oct. 3, 2022, the disclosure of which is incorporated by reference herein in its entirety, including any drawings.

BACKGROUND

The effect and efficacy of insertion of an exogenous nucleic acid sequence, e.g., a gene of interest, in a biological particle's genomic nucleic acids (e.g., genomic nucleic acids from a cell or a cell nucleus) is highly dependent on its insertion site in the biological particle's genome. Insertion site may effect expression level of the exogenous nucleic acid sequence. Insertion site may also disrupt and/or interrupt expression of one or more of the biological particle's endogenous genes. In the context of immune cells modified to express chimeric antigen receptors (CARs), broad correlations have been found between the longevity of CAR-modified immune cells in treated patients and the insertion site of the exogenous, CAR-encoding gene, in the modified cells' DNA.

Currently, techniques are available that can assay sequence and expression level of exogenous genes, e.g., CARs, inserted in cells', e.g., B or T cells', genomes at the single cell level. Techniques are not, however, available to assay insertion sites of the exogenous, e.g., CAR, genes in an individual cell's genomic DNA, e.g., at the single cell level. Instead, current techniques assay trends in exogenous genes' insertion sites within a population of cells, e.g., at a cell population-level.

There is a need for high-throughput methods and reagents that reliably and rapidly characterize and identify insertion sites of exogenous nucleic acids, such as a gene of interest, in a biological particle's genomic, e.g., endogenous, nucleic acids.

SUMMARY

The present disclosure provides, inter alia, compositions, methods and systems for the characterization of a biological particle, e.g., cell or nucleus, modified to include an exogenous nucleic acid, e.g., gene of interest, inserted in its genomic. e.g., endogenous, nucleic acids. The compositions, methods and systems described herein may characterize the biological particle by identifying the insertion site of the exogenous nucleic acid in its genomic nucleic acids. The identification of the insertion site of the exogenous nucleic acid in the biological particle's genomic nucleic acids may identify the biological particle as suitable for administration to a subject. The identification of the insertion site of the exogenous nucleic acid in the biological particle's genomic nucleic acids may also, or alternatively, characterize the effect of the exogenous nucleic acid's insertion site on expression of the exogenous nucleic acids and/or expression of the biological particle's endogenous genes.

In the methods, a partition is provided. The partition includes (i) a biological particle including a heterologous nucleic acid molecule. The heterologous nucleic acid molecule includes an exogenous insert and endogenous flanking sequences that flank the exogenous insert. The partition further includes (ii) a plurality of nucleic acid barcode molecules having a partition-specific barcode sequence and a capture sequence; (iii) a first insert primer having, from 5' to 3', a splinting sequence and a sequence complementary to a first sequence of the exogenous insert; and (iv) a splint oligonucleotide having a sequence complementary to the capture sequence of a first nucleic acid barcode molecule of the plurality of nucleic acid barcode molecules and a sequence complementary to the splinting sequence of the first insert primer. The partition is subjected to conditions sufficient for: (i) coupling the first nucleic acid barcode molecule to the first insert primer to generate a barcoded first insert primer; and (ii) hybridizing the barcoded first insert primer to the first sequence of the exogenous insert of the heterologous nucleic acid molecule. A first barcoded nucleic acid molecule is generated. The first barcoded nucleic acid molecule includes: (i) the partition-specific barcode sequence, or a reverse complement thereof, and (ii) a first endogenous flanking sequence of the endogenous genomic flanking sequences, or a reverse complement thereof.

In some embodiments, the heterologous nucleic acid molecule comprises a double-stranded deoxyribonucleic acid (dsDNA) molecule.

In some embodiments, the exogenous insert comprises a recognition site for a restriction enzyme (RE), wherein the recognition site is at a 5' or 3' end of the exogenous insert. In some embodiments, the recognition site for the RE differs from the cleavage site for the RE.

In some embodiments, the conditions are further sufficient for denaturing the dsDNA molecule.

In some embodiments, the coupling the first nucleic acid barcode molecule to the first insert primer comprises hybridizing: (i) the first nucleic acid barcode molecule to the splint oligonucleotide; and (ii) the first insert primer to the splint oligonucleotide. In some embodiments. (i) the sequence complementary to the capture sequence of the first nucleic acid barcode molecule of the splint oligonucleotide hybridizes to the capture sequence of the first nucleic acid barcode molecule; and (ii) the sequence complementary to the splinting sequence of the splint oligonucleotide hybridizes to the splinting sequence of the first insert primer.

In some embodiments, the coupling the first nucleic acid barcode molecule to the first insert primer comprises ligating the first nucleic acid barcode molecule to the first insert primer. In some embodiments, the ligating is performed by an enzyme capable of nick repair. In some embodiments, the enzyme comprises a ligase or polymerase. In some embodiments, the enzyme comprises a DNA polymerase, a reverse transcriptase, or a DNA ligase.

In some embodiments, the hybridizing the barcoded first insert primer to the first sequence of the exogenous insert of the heterologous nucleic acid molecule is by complementary base pairing.

In some embodiments, the method includes extending the barcoded first insert primer hybridized to the first sequence of the exogenous insert of the heterologous nucleic acid molecule into the first endogenous flanking sequence to produce the first barcoded nucleic acid molecule. In some embodiments, the method further includes extending the barcoded first insert primer hybridized to the first sequence of the exogenous insert of the heterologous nucleic acid molecule into the first endogenous flanking sequence by a polymerase to produce the first barcoded nucleic acid molecule. In some embodiments, the polymerase is a high fidelity polymerase or a hot start polymerase.

In some embodiments, the method includes extending the barcoded first insert primer hybridized to the first sequence of the exogenous insert of the heterologous nucleic acid molecule into the first endogenous flanking sequence over multiple cycles to yield multiple copies of the first barcoded nucleic acid molecule.

In some embodiments, the method includes fragmenting the first barcoded nucleic acid molecule hybridized to the first endogenous flanking sequence to yield a barcoded fragment of the first barcoded nucleic acid molecule.

In some embodiments, the method further includes subjecting the first barcoded nucleic acid molecule to second strand synthesis to yield a double stranded (ds) derivative of the first barcoded nucleic acid molecule. In some embodiments, the second strand synthesis comprises polymerizing a complementary strand to the first barcoded nucleic acid molecule using a random primer. In some embodiments, the method includes fragmenting the ds derivative of the first barcoded nucleic acid molecule to yield a barcoded fragment thereof.

In some embodiments, the fragmenting is performed by a RE. In some embodiments, the RE is a type I or type II RE.

In some embodiments, the method further includes attaching a first adaptor to the first barcoded nucleic acid molecule, or a derivative, or amplicon, or a barcoded fragment thereof to generate an adapted barcoded product, wherein the first adaptor comprises a reverse primer binding site. In some embodiments, the attaching is by ligating. In some embodiments, the method further includes amplifying the adapted barcoded product with a first primer that hybridizes to the reverse primer-binding site. In some embodiments, the plurality of nucleic acid barcode molecules further comprise a forward primer binding site or reverse complement thereof, and wherein the amplifying further comprises amplifying with a second primer that hybridizes to the forward primer binding site.

In some embodiments, the sequence complementary to the first sequence of the exogenous insert is within about 20 to 50 nucleotides of the junction of the exogenous insert and the first endogenous flanking sequence. In some embodiments, the exogenous insert comprises a recognition site for an RE, wherein the recognition site is: (i) in the sequence complementary to the first sequence of the exogenous insert of the first insert primer, or (ii) between the sequence complementary to the first sequence of the exogenous insert of the first primer and the junction of the exogenous insert and the first endogenous flanking sequence. In some embodiments, the recognition site for the RE differs from the cleavage site for the RE, and wherein the RE cleavage site is in the first endogenous flanking sequence.

In some embodiments, the exogenous insert encodes a polypeptide or a functional RNA. In some embodiments, the exogenous insert encodes the polypeptide. In some embodiments, the polypeptide comprises a chimeric antigen receptor, brain-derived neurotrophic factor, hemoglobin (β-chain), adenosine deaminase, p53, dystrophin, alpha-galactosidase A, Factor VIII, Factor IX, lipoprotein lipase or acid alpha-glucosidase.

In some embodiments, the method further includes determining expression of an analyte of the biological particle, optionally wherein the analyte is encoded by the exogenous insert. In some embodiments, the determining expression is of an mRNA analyte. In some embodiments, expression of the mRNA analyte is determined via generation of a second barcoded nucleic acid molecule, wherein the second barcoded nucleic acid molecule comprises: (i) the partition-specific barcode sequence, or a reverse complement thereof; and (ii) at least a portion of a nucleic acid sequence of the mRNA analyte, or a reverse complement thereof. In some embodiments, the plurality of nucleic acid barcode molecules further comprises a second nucleic acid barcode molecule comprising the partition-specific barcode sequence and a second capture sequence. In some embodiments, the second capture sequence is configured to couple to: (a) the mRNA analyte or (b) non-templated nucleotides appended to a cDNA reverse transcribed from the mRNA analyte. In some embodiments, the second capture sequence is configured to couple to (a) the mRNA analyte. In some embodiments, the second capture sequence configured to couple to the mRNA analyte comprises: a polyT sequence, a sequence complementary to a specific sequence of the mRNA analyte, or a random sequence. In some embodiments, the second capture sequence is configured to couple to (b) the non-templated nucleotides appended to a cDNA reverse transcribed from the mRNA analyte. In some embodiments, the mRNA analyte is reverse transcribed to the cDNA utilizing a primer comprising: a polyT sequence, a sequence complementary to a specific sequence of the mRNA analyte or a random sequence. In some embodiments, the non-templated nucleotides appended to the cDNA comprise a cytosine. In some embodiments, the second capture sequence configured to couple to the cDNA comprises a guanine. In some embodiments, coupling of the capture sequence to the non-templated cytosine extends reverse transcription of the cDNA into the second nucleic acid barcode molecule to generate the second barcoded nucleic molecule.

In some embodiments, the second nucleic acid barcode molecule further comprises a template switch oligonucleotide (TSO).

In some embodiments, the determining expression is of a peptide or protein analyte. In some embodiments, the expression of the peptide or protein analyte is determined by: further providing in the partition, a labeling agent operatively coupled to a first reporter oligonucleotide, wherein the labeling agent binds the peptide or protein analyte. In some embodiments, the first reporter oligonucleotide comprises a first reporter barcode sequence and a capture handle sequence. In some embodiments, the plurality of nucleic acid barcode molecules further comprises a further nucleic acid barcode molecule comprising the partition-specific barcode sequence and a further capture sequence. In some embodiments, the further capture sequence is configured to couple to the capture handle sequence.

In some embodiments, the method further includes generating a further barcoded nucleic acid molecule wherein the further barcoded nucleic acid molecule comprises: (i) the partition-specific barcode sequence, or a reverse complement thereof, and (ii) the first reporter barcode sequence, or a reverse complement thereof. In some embodiments, the further barcoded nucleic acid molecule is used to determine expression of the peptide or protein analyte.

In some embodiments, expression of the peptide or protein analyte is determined by fluorescence activated cell sorting (FACS), wherein the FACS is performed using a labeling agent comprising a fluorescent molecule, wherein the labeling agent binds the peptide or protein analyte. In some embodiments, the FACS detects biological particles comprising the fluorescent molecule as biological particles expressing the peptide or protein analyte. In some embodiments, the biological particle is provided in the partition following selection for comprising the fluorescent molecule by FACS.

In some embodiments, the method further includes determining a sequence of the first endogenous flanking sequence of the first barcoded nucleic acid molecule. In some embodiments, the method further includes mapping the exogenous insert as inserted into a location in endogenous sequences of the biological particle based on the determined sequence of the first endogenous flanking sequence. In some embodiments, the biological particle is characterized as comprising the exogenous insert at the location in the endogenous sequences. In some embodiments, the method further includes identifying the location as capable of dysregulating expression of one or more endogenous genes of the biological particle, wherein the identifying comprises determining the biological particle is unsuitable for administration as a therapeutic agent to a subject in need thereof. In some embodiments, the dysregulating comprises: (i) activation of an adjacent endogenous gene, wherein the adjacent endogenous gene comprises an oncogene; (ii) interruption of an endogenous gene; or (iii) silencing an endogenous gene.

In some embodiments, the biological particle is a cell or a nucleus of a cell. In some embodiments, the cell is a T cell, bone marrow progenitor cell, an induced progenitor stem cell, a plasma cell or a retinal cell. In some embodiments, the cell is for administration to a subject. In some embodiments, the cell is autologous or allogeneic to the subject. In some embodiments, the cell has been modified to comprise the heterologous nucleic acid by a viral vector. In some embodiments, the viral vector is an adeno-associated virus vector or a retrovirus vector.

In some embodiments, the cell has been modified to comprise the exogenous insert by a gene editing protein having sequence-specific integration characteristics. In some embodiments, the gene editing protein is a zinc finger protease, a transcription activator-like effector nuclease (TALEN) or an RNA-guided endonuclease. In some embodiments, the RNA-guided endonuclease is a Cas protein. In some embodiments, the Cas protein is a Cas 9 protein.

In some embodiments, the cell is characterized as comprising on-target insertion of the exogenous insert if the first endogenous flanking sequence reflects the sequence-specific integration characteristics of the gene editing protein.

In some embodiments, the cell is characterized as comprising off-target insertion of the exogenous insert if the first endogenous flanking sequence does not reflect the sequence-specific integration characteristics of the gene editing protein.

In some embodiments, the partition is a well, microwell or droplet.

In some embodiments, the disclosure provides for a system that implements the methods of the disclosure. In other embodiments, the disclosure provides for a composition that may be employed in the methods of the disclosure. In yet other embodiments, the disclosure provides for kits, e.g., kits which may include a composition of the disclosure in combination with instructions for use thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

As shown in FIG. 10C, the barcoded fragment, to which the adaptors may have been ligated, may then be amplified using a first primer, e.g., reverse primer that hybridizes to the reverse primer binding site of the adaptor and as second primer, e.g., a forward primer having a sequence that hybridizes to a corresponding to a sequence of the barcoded first primer.

DETAILED DESCRIPTION OF THE DISCLOSURE

Figure 1:
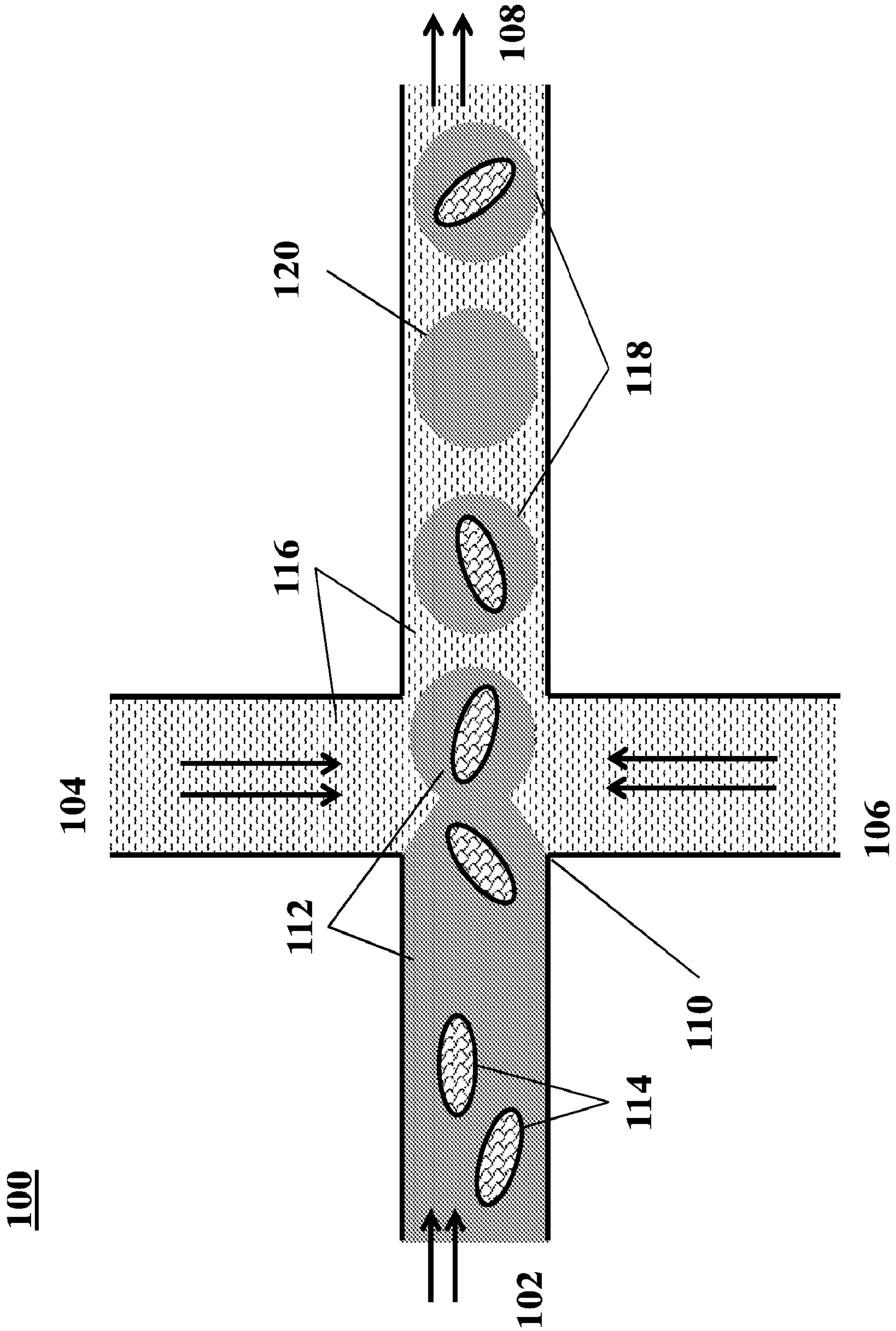
FIG. 1 shows an exemplary microfluidic channel structure for partitioning individual analyte carriers.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise. "A and/or B" is used herein to include all of the following alternatives: "A", "B", "A or B", and "A and B".

Whenever the term "at least." "greater than," or "greater than or equal to" precedes the first numerical value in a series of two or more numerical values, the term "at least." "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than." or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

Headings, e.g., (a), (b), (i) etc., are presented merely for case of reading the specification and claims. The use of headings in the specification or claims does not require the steps or elements be performed in alphabetical or numerical order or the order in which they are presented.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, the use of these terms in the specification does not by itself connote any required priority, precedence, or order.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses). The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing." as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead." as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. The nucleic acid barcode molecule may be coupled to or attached to the nucleic acid molecule comprising the nucleic acid sequence. For example, a nucleic acid barcode molecule described herein may be hybridized to an analyte (e.g., a messenger RNA (mRNA) molecule) of a cell. Reverse transcription can generate a barcoded nucleic acid molecule that has a sequence corresponding to the nucleic acid sequence of the mRNA and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction may be performed prior to, during, or following barcoding of the nucleic acid sequence to generate the barcoded nucleic acid molecule. For example, the nucleic acid molecule comprising the nucleic acid sequence may be subjected to reverse transcription and then be attached to the nucleic acid barcode molecule to generate the barcoded nucleic acid molecule, or the nucleic acid molecule comprising the nucleic acid sequence may be attached to the nucleic acid barcode molecule and subjected to a nucleic acid reaction (e.g., extension, ligation) to generate the barcoded nucleic acid molecule. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the nucleic acid molecule (e.g., mRNA).

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a check swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle" may be used herein to generally refer to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a nucleus of a cell. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag." as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition can be a physical container, compartment, or vessel, such as a droplet, a flowcell, a reaction chamber, a reaction compartment, a tube, a well, or a microwell. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Overview

Provided herein, inter alia, are compositions, methods, kits and systems providing for the characterization of a biological particle that has been modified to include an exogenous nucleic acid, e.g., gene of interest, inserted in its endogenous, e.g., genomic, nucleic acids. The method, kits and systems may characterize the modified biological particle by identifying where, in its endogenous nucleic acids, insertion of the exogenous nucleic acid has taken place.

Figure 8A:
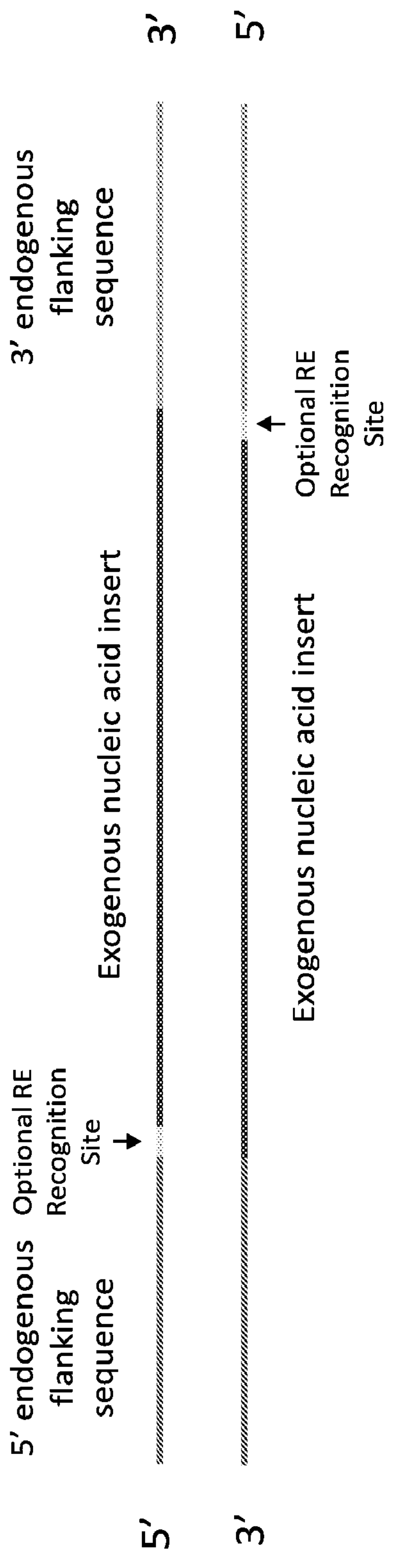
FIG. 8A schematically depicts an exogenous sequence inserted into a genome at an insertion site.
Figure 8B:
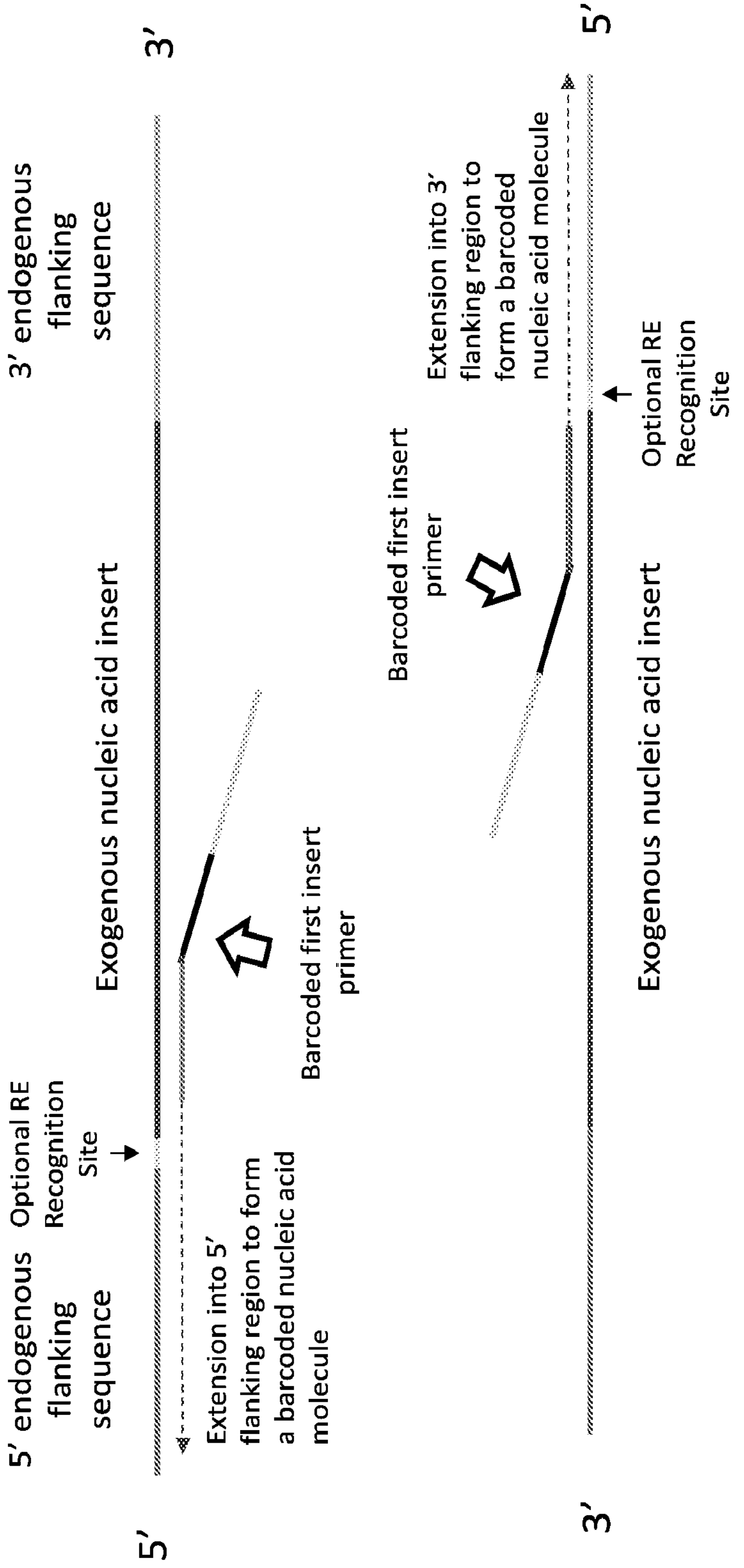
FIG. 8B schematically depicts formation of a barcoded nucleic acid molecule from the barcoded first insert primer, e.g., prepared as shown in FIG. 7. In the formation of the barcoded nucleic acid molecule, the first insert primer is hybridized to a nucleotide sequence of an exogenous nucleic acid insert that has integrated in a biological particle's genomic, endogenous, nucleic acids. The first insert primer, hybridized to the nucleotide sequence of the exogenous nucleic acid insert, is extended into the biological particle's endogenous nucleic acids flanking the exogenous nucleic acid insert. The upper and lower depictions show hybridization to, and subsequent extension of, the barcoded first insert primer into the biological particle's 5' or 3', respectively, flanking endogenous nucleic acids. The extension of the barcoded first insert primer into the biological particle's endogenous nucleic acids forms the barcoded nucleic acid molecule. While generation of a single barcoded nucleic acid molecule is depicted in FIG. 8, multiple barcoded nucleic acid molecules may be generated by multiple (e.g., first, second, third, fourth, fifth, etc.) cycles of hybridizing a (e.g., first, then second, then third, then fourth, then fifth, etc.) barcoded first insert primer to the first sequence of the exogenous insert and extending the (e.g., first, then second, then third, then fourth, then fifth, etc.) barcoded first insert primer into the first endogenous flanking sequence flanking the insert. Also as depicted in FIG. 8, a restriction enzyme recognition site may be present in one or both, e.g., 5' and/or 3', ends of the exogenous insert.
Figure 9:
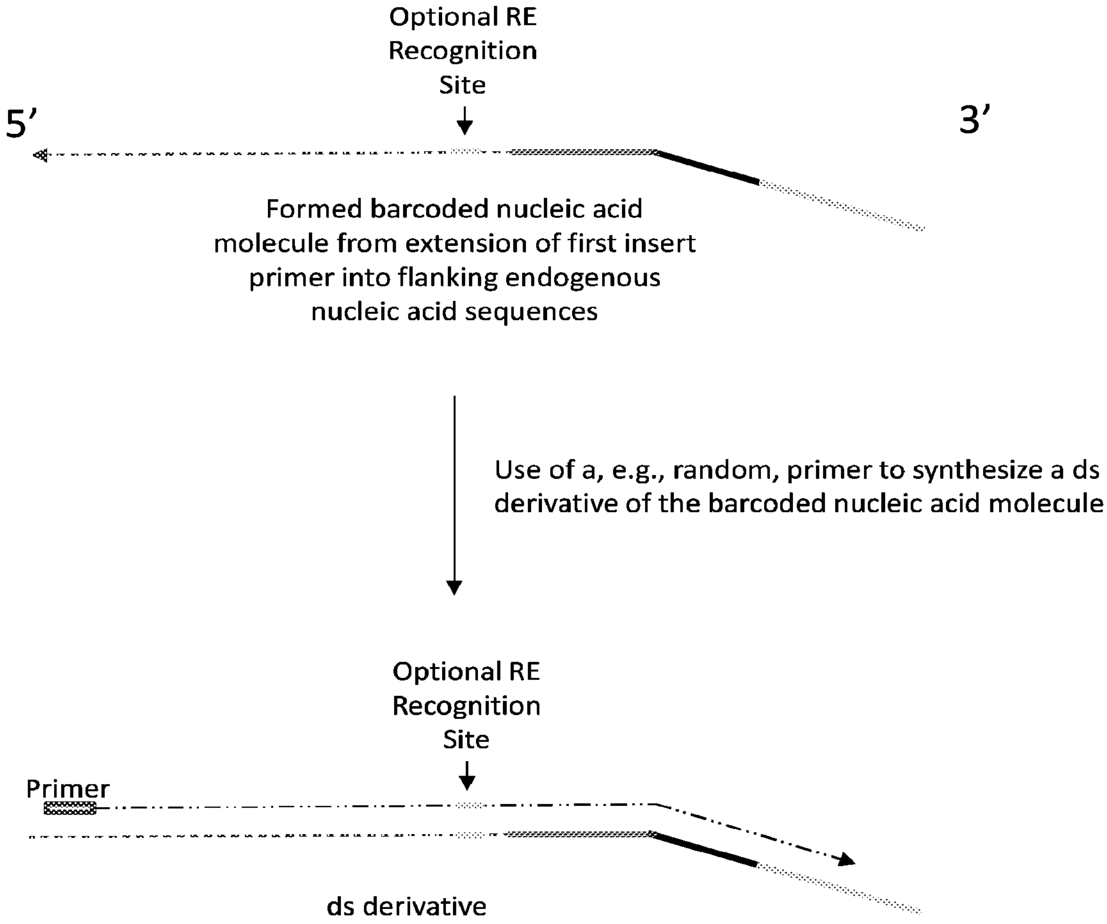
FIG. 9 schematically depicts preparation of a double-stranded (ds) derivative of the barcoded nucleic acid molecule prepared in FIG. 8. In an embodiment, the ds derivative is prepared by hybridizing a primer, e.g. random primer, to the barcoded nucleic acid molecule and polymerizing a second strand, e.g., complementary to the barcoded nucleic acid molecule, using the primer.
Figure 10A:
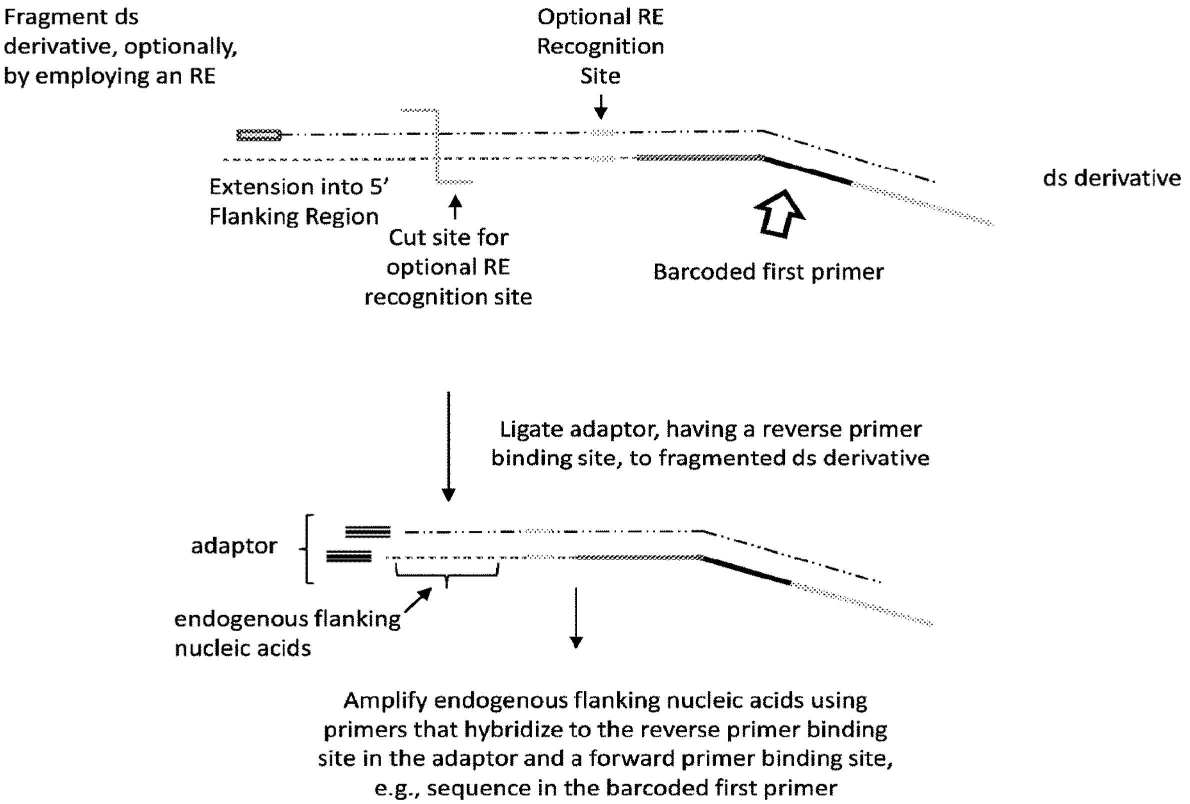
FIG. 10A schematically depicts examples of processing steps that may be performed to prepare a ds derivative, as shown in FIG. 9, for further, e.g. sequencing, analysis. Example steps include fragmenting the ds derivative. In some embodiments, the fragmenting may be performed by cleaving the ds derivative with a restriction enzyme, e.g., whose recognition site may be at the 5' and/or 3' end of the exogenous nucleic acid insert and whose cut site is in the flanking endogenous nucleic acids flanking the exogenous nucleic acid insert. In other embodiments, the fragmenting may be performed by a fragmenting enzyme. Fragments of the ds derivative may have ends that permit the ligation of adaptors, which may include a reverse primer binding site. The fragments of the ds derivative, to which the adaptors may have been ligated, may then be amplified using a first primer, e.g., reverse primer that hybridizes to the reverse primer binding site of the adaptor and as second primer, e.g., a forward primer having a sequence that hybridizes to a sequence of the barcoded first primer.
Figure 10B:
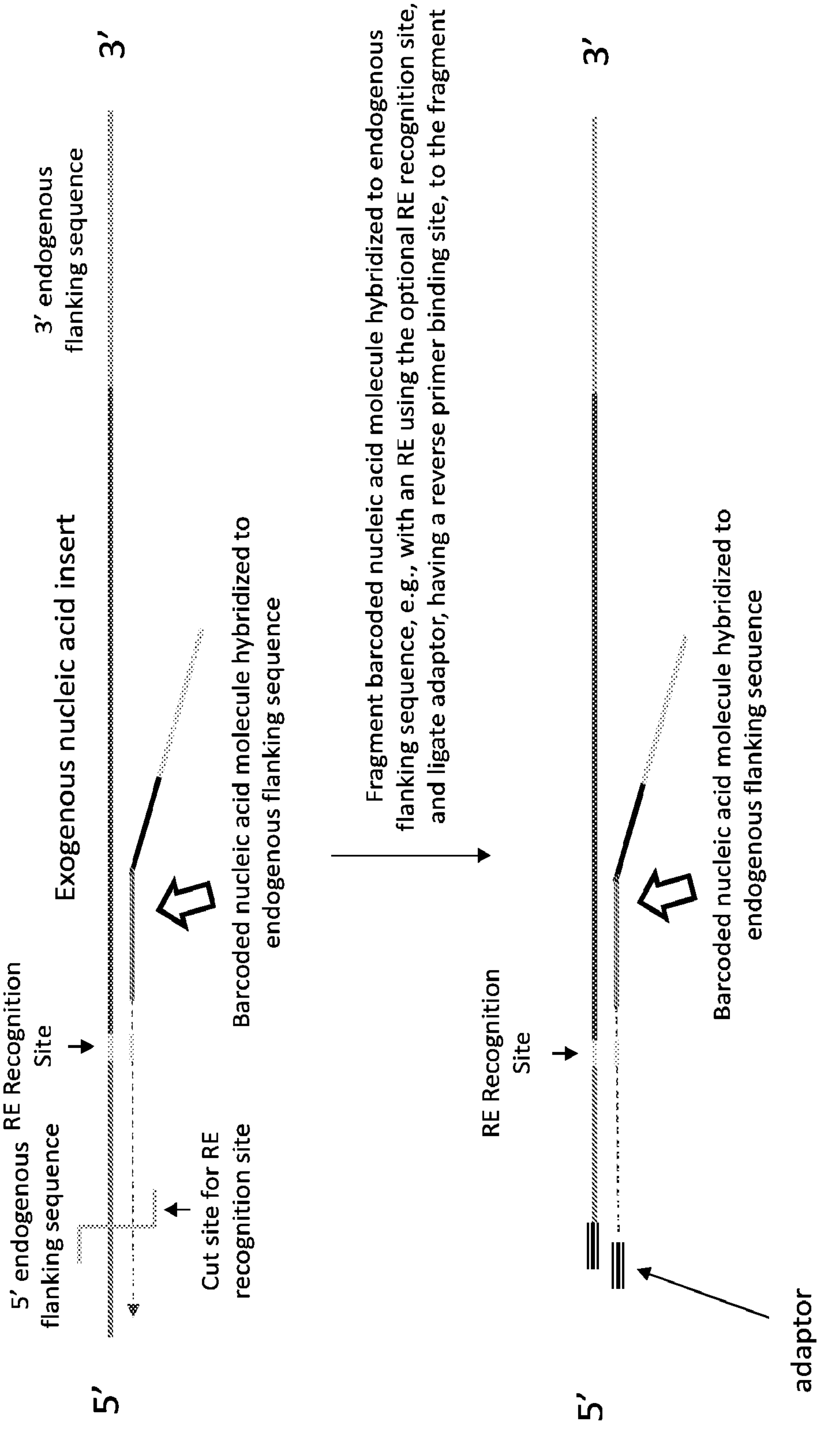
FIG. 10B and FIG. 10C schematically depict examples of optional processing steps that may be performed on a barcoded nucleic acid molecule hybridized to the first endogenous flanking sequence (e.g., as also shown in FIG. 8), prior to further, e.g. sequencing, analysis. Example steps depicted in FIG. 10B include fragmenting the barcoded nucleic acid molecule while hybridized to the first endogenous flanking sequence to yield a barcoded fragment of a barcoded nucleic acid molecule. In some embodiments, the fragmenting may be performed with a restriction enzyme, e.g., whose recognition site may be at 5' and/or 3' end of the exogenous nucleic acid insert and whose cut site is in the flanking endogenous nucleic acids flanking the exogenous nucleic acid insert. In other embodiments, the fragmenting may be performed by a fragmenting enzyme. The barcoded fragment of the barcoded nucleic acid molecule may have ends that permit the ligation of adaptors, which may include a reverse primer binding site.
Figure 10C:
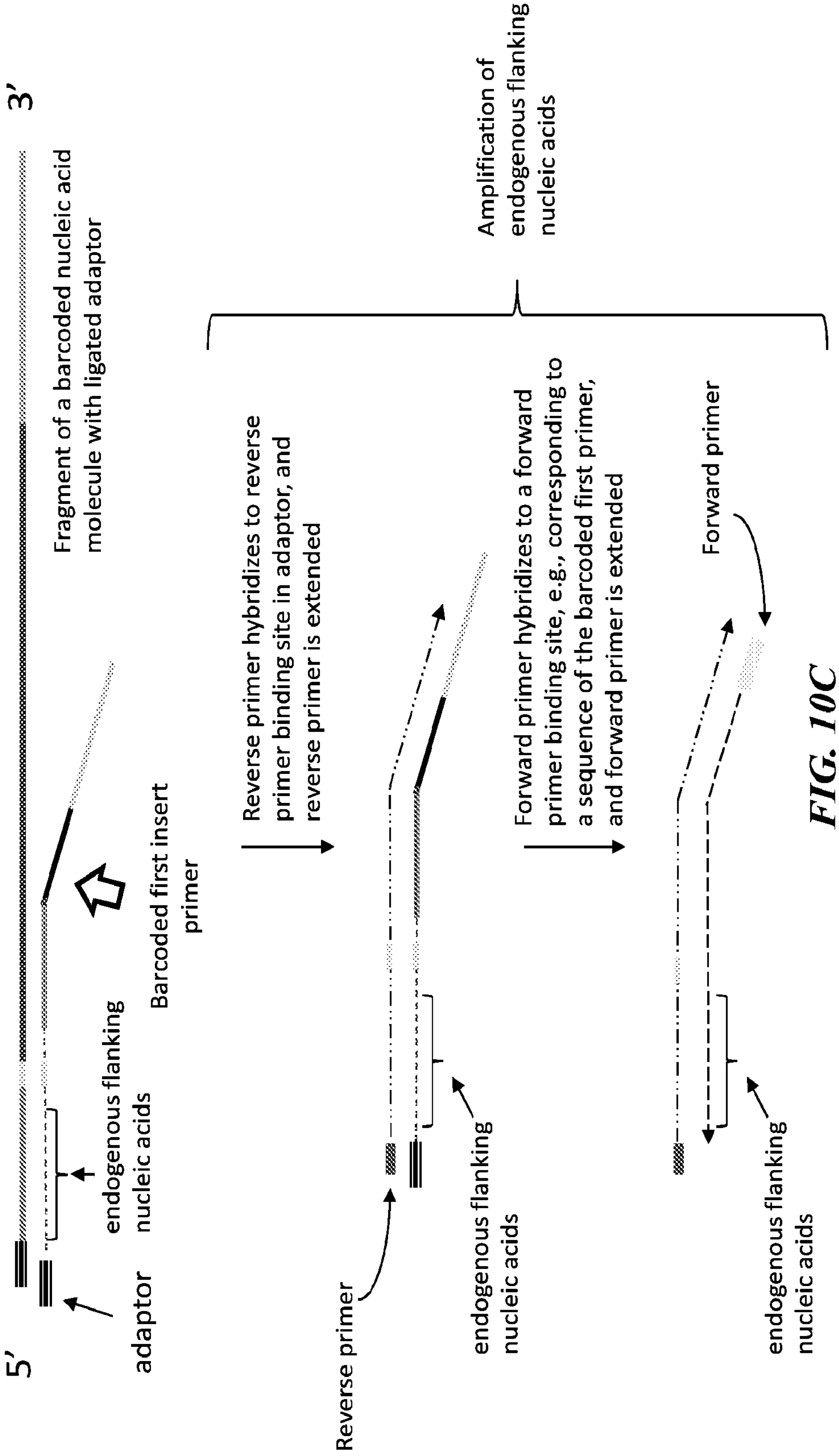

FIG. 8A schematically depicts insertion of an exogenous nucleic acid, e.g., gene of interest, into a genome of a biological particle (e.g., a cellular genome, a genome of a nucleus). As the effect and efficacy of the inserted exogenous nucleic acid can vary depending on the gene insertion site, the determination of the insertion loci (e.g., the endogenous flanking sequences) at the single cell or single nucleus level can improve the field of cell and gene therapy. For example, the identification of the insertion site is important in the optimization of cell-based therapeutics, such as immune cells modified to express chimeric antigen receptors, e.g., CAR-T cells, to treat cancer. The ability to identify the insertion site of an exogenous nucleic acid in endogenous nucleic acids of such a modified biotherapeutic cell, e.g., CAR-T cell, can confirm the modified cell is likely both safe, e.g., the exogenous nucleic acid has not inserted at a location that will alter products or expression levels of the modified cell's endogenous genes, and maximally effective, e.g., has inserted at a location in which it will be expressed at sufficient levels and over a sufficient length of time, prior to its administration.

The identification of the insertion site of an exogenous nucleic acid in a biological particle's endogenous e.g., genomic, nucleic acids is also of particular importance in instances in which the exogenous nucleic acids are inserted in the biological particle's genome by a gene editing protein having sequence-specific integration characteristics. In such instances, it will be advantageous to ensure that the exogenous nucleic is inserted in the biological particle's endogenous. e.g., genomic, nucleic acids at its expected site, e.g., sequence consistent with the gene editing protein's sequence-specific integration characteristics.

In addition, methods that can link the determined insertion loci with transcriptomic and multi-analyte information at the single cell or single nucleus level can beneficially yield better insights and advances in cell and gene therapy. Therefore, there exists a need for improved methods, kits, compositions, and systems that enable the determination of insertion loci at the single cell or single nucleus level.

Methods of the Disclosure

As described in more detail below, the disclosure relates to approaches, methods, compositions, kits and systems for the characterization of biological particles modified by the insertion of exogenous nucleic acids in their endogenous, e.g., genomic, nucleic acids. This characterization may identify the insertion site of the exogenous nucleic acid in the biological particle's endogenous, e.g., genomic, nucleic acids. The identification of the insertion site of the exogenous nucleic acid may further, or alternatively, identify the biological particle as suitable for administration to a subject. The identification of the insertion site may further, or alternatively, characterize effects of the insertion site on expression of the exogenous nucleic acid, and/or the biological particle's endogenous genes.

In some embodiments, methods, kits, compositions, and systems of the disclosure advantageously provide insertion loci information at the single biological particle (e.g., single cell or single nucleus) level via the provision of barcoded insert primers for associating partition barcodes with the sequences that flank the exogenous insert.

In any of the methods provided herein, a partition may be provided. The partition may be a well, a microwell, or a droplet. Partitions and characteristics thereof are further described herein in the section entitled "SYSTEMS AND METHODS FOR SAMPLE COMPARTMENTALIZATION". The provided partition may include: (i) a biological particle having a heterologous nucleic acid molecule; (ii) a plurality of nucleic acid barcode molecules; (iii) a first insert primer; and (iv) a splint oligonucleotide. In some embodiments, of the methods provided herein, the partition may be subjected to conditions sufficient for: (i) coupling the first nucleic acid barcode molecule to the first insert primer to generate a barcoded first insert primer; and (ii) hybridizing the barcoded first insert primer to the first sequence of the exogenous insert of the heterologous nucleic acid molecule. A first barcoded nucleic acid molecule may be generated. The first barcoded nucleic acid molecule may include: (i) the partition-specific barcode sequence, or a reverse complement thereof, and (ii) a first endogenous flanking sequence of the endogenous genomic flanking sequences, or a reverse complement thereof.

In some embodiments, the biological particle in the provided partition may be a cell. In other embodiments, the biological particle may be a cell derivative or an organelle of a cell, e.g., nucleus. The biological particle may be any type of cell, or the derivative or organelle of any type of cell, e.g., a prokaryotic, eukaryotic, bacterial, fungal, plant, mammalian, or other type of animal cell. In some instances, the biological particle may be an immune cell, a derivative of an immune cell, or an organelle, e.g., nucleus, of an immune cell, such as a T cell or B cell. In other instances, the biological particle may be a stem or progenitor cell, a derivative of a stem or progenitor cell, or an organelle, e.g., nucleus, of a stem or progenitor cell, such as a hematopoetic stem cell. In yet other instances, the biological particle may be a retinal cell, a derivative of a retinal cell, or an organelle, e.g., nucleus, of a retinal cell.

The biological particle in the provided partition may be a cell, derivative of a cell or organelle of a cell that had been obtained from a sample of a subject. The biological particle, e.g., cell or cell nucleus, may have been obtained from a tissue of a subject by biopsy, core biopsy, needle aspirate, or fine needle aspirate. In some instances, the biological particle, e.g., cell or cell nucleus, may have been obtained from a fluid sample of the subject, such as a blood sample. The biological particle may have been processed from the sample. The processing of the sample may have included steps such as filtration, selective precipitation, purification, centrifugation, agitation, heating, and/or other processes. For example, a sample may have been filtered to remove a contaminant or other materials. In some cases, biological particles, such as cells or cell nuclei, of a sample may have been processed to separate and/or sort biological particles, e.g., cells or cell nuclei, of different types, e.g., by FACS or MACS based on an expressed surface markers. A separation process may be a positive selection process, a negative selection process (e.g., removal of one or more biological particle types and retention of one or more other biological particle types of interest), and/or a depletion process (e.g., removal of a single biological particle type from a sample). A biological particle obtained from a subject e.g., a sample such as a tissue sample, may be modified to include the exogenous insert and used as a therapeutic. The biological particle, once modified to include the exogenous insert, may be administered to the subject from which the biological particle was obtained, e.g., autologous to the subject, or administered to a second subject of the same species of the subject, e.g., allogeneic to the subject.

The biological particle. e.g., cell, cell derivative or cell organelle, in the provided partition may include a heterologous nucleic acid molecule. The heterologous nucleic acid molecule may include an exogenous insert, e.g., exogenous nucleic acids, and endogenous, e.g., genomic, flanking sequences that flank the exogenous insert. In some embodiments, the heterologous nucleic acid molecule, including the exogenous insert and endogenous flanking sequences flanking the insert, may be a double-stranded deoxyribonucleic acid (dsDNA) molecule. In other embodiments, it may be either a single-stranded DNA (ssDNA) or single-stranded ribonucleic acid (ssRNA) molecule.

The exogenous insert of the heterologous nucleic acid molecule may include a nucleic acid sequence that encodes a polypeptide or a functional RNA. In embodiments in which the exogenous insert includes nucleic acids encoding a polypeptide, the polypeptide may be a full-length protein or a portion of a full-length protein. In some embodiments, the exogenous nucleic acids may encode a protein or a portion of a protein that is at least 20 amino acid residues, at least 40 amino acid residues, at least 60 amino acid residues, at least 80 amino acid residues, at least 100 amino acid residues, at least 200 amino acid residues, at least 300 amino acid residues, at least 400 amino acid residues, at least 500 amino acid residues, at least 600 amino acid residues, at least 700 amino acids, at least 800 amino acid residues, at least 900 amino acid residues, at least 1000 amino acid residues, at least 1100 amino acid residues, at least 1200 amino acid residues, at least 1300 amino acid residues, up to 40 amino acid residues, up to 60 amino acid residues, up to 80 amino acid residues, up to 100 amino acid residues, up to 200 amino acid residues, up to 300 amino acid residues, up to 400 amino acid residues, up to 500 amino acid residues, up to 600 amino acid residues, up to 700 amino acids, up to 800 amino acid residues, up to 900 amino acid residues, up to 1000 amino acid residues, up to 1100 amino acid residues, up to 1200 amino acid residues, or up to 1300 amino acid residues in length.

In some embodiments, the exogenous insert of the heterologous nucleic acid molecule may include nucleic acids encoding a protein or a portion of a protein that is one domain, at least one domain, two domains, at least two domains, three domains, at least three domains, four domains, at least four domains, five domains, at least five domains, six domains, at least six domains, seven domains, at least seven domains, eight domains, at least eight domains, nine domains, at least nine domains, ten domains, at least ten domains, at least thirty domains, at least forty domains, at least fifty domains, at least sixty domains, at least seventy domains, at least eighty domains, at least ninety domains or at least one hundred domains. The target antigen may be an antigen that includes at most two hundred domains, at most 175 domains, at most 150 domains, at most 125 domains, at most 100 domains, at most 75 domains, at most 50 domains, at most 25 domains, at most 20 domains, at most 15 domains, at most 10 domains, or at most 5 domains.

The protein, all or a portion of which may be encoded by nucleic acids of the exogenous insert may be an investigational protein or a therapeutic protein. Examples of therapeutic proteins that may be encoded by nucleic acids of the exogenous insert, include chimeric antigen receptors, brain-derived neurotrophic factor, hemoglobin (β-chain), adenosine deaminase, p53, dystrophin, alpha-galactosidase A, Factor VIII, Factor IX, lipoprotein lipase, alpha 1-antitrypsin or acid alpha-glucosidase. In embodiments in which the exogenous insert includes nucleic acids encoding a therapeutic protein, the biological particle including the exogenous insert may be for administration to the subject.

In some embodiments, the exogenous insert of the heterologous nucleic acid molecule may include nucleic acid sequences in addition those encoding the polypeptide or functional RNA. These sequences may include a restriction enzyme (RE) recognition site. Such a RE recognition site may be included at a 5' end or 3' end of the exogenous insert. An RE recognition site at a 5' or 3' end of the exogenous insert may be located about 0 to 50 nucleotides from the junction between the exogenous insert and an endogenous flanking sequence flanking the exogenous insert, or it may be about 0 to 46 nucleotides, or about 0 to 42 nucleotides, or about 0 to 438 nucleotides, or about 0 to 34 nucleotides, or about 0 to 30 nucleotides, or about 0 to 26 nucleotides, or about 0 to 22 nucleotides, or about 0 to 18 nucleotides, or about 0 to 14 nucleotides, or about 0 to 10 nucleotides, or about 50 nucleotides, or about 45 nucleotides, or about 40 nucleotides, or about 35 nucleotides, or about 30 nucleotides, or about 25 nucleotides, or about 20 nucleotides, or about 15 nucleotides or about 10 nucleotides, from the junction between the exogenous insert and an endogenous flanking sequence flanking the exogenous insert. In some embodiments, the exogenous insert of the heterologous nucleic acid may include RE recognition sites at both 5' and 3' end of the exogenous insert. In such instances the RE recognition site at the 5' end of the exogenous insert and the RE recognition site at 3' end of the exogenous insert may be for the same RE. In other such instances, the RE recognition site at the 5' end of the exogenous insert may be for a different RE than the RE recognition site at 3' end of the exogenous insert.

RE recognition sites may be for a type I or type II RE. In some embodiments, the RE whose recognition site is at a 5' and/or 3' end of the exogenous insert may be an RE that has a cleavage site at a location different from that of its recognition site in the exogenous insert. In such embodiments, the RE may have a recognition site at a 5' or 3' end of the exogenous insert and a cleavage site in an endogenous flanking sequence flanking the exogenous insert. In such certain aspects, the RE may have a recognition site at a 5' or 3' end of the exogenous insert and a cleavage site in the endogenous flanking sequence that flanks the exogenous insert that may be about 10 to 1000 nucleotides, or within about 10 to 900 nucleotides, or within about 10 to 800 nucleotides, or within about 10 to 700 nucleotides, or within about 10 to 600 nucleotides, or within about 10 to 500 nucleotides, or within about 10 to 400 nucleotides, or within about 10 to 300 nucleotides, or within about 10 to 200 nucleotides, or within about 10 to 100 nucleotides, or within about 10 to 50 nucleotides from the junction of endogenous flanking sequence and the exogenous insert. In other certain such embodiments, the RE may have a recognition site at a 5' or 3' end of the exogenous insert and a cleavage site in the immediately flanking endogenous flanking sequence within about 10 to 40, or about 10 to 35, or about 10 to 30, or about 10 to 25, or about 10 to 20 nucleotides from the exogenous insert. Non-limiting examples of REs that have a recognition site at a location different from their cleavage site include AcuI, BsgI, BpmI, BpuEI, EcoP151, MmeI, and NmeAIII.

The exogenous insert may have been inserted in the endogenous nucleic acids of the biological particle via introduction with a viral vector or a gene editing protein. Examples of viral vectors include retroviruses, such as lentiviruses, adeno-associated viruses and adenoviruses. Gene editing proteins that may insert an exogenous nucleic acid in endogenous, e.g., genomic, nucleic acids of a biological particle may have random or have sequence-specific integration characteristics. Examples of gene editing proteins having sequence-specific integration characteristics include, but are not limited to, zinc finger proteases, transcription activator-like effector nucleases (TALENs) and RNA-guided endonucleases. RNA-guided endonucleases that may be used to insert exogenous nucleic acids in endogenous, e.g., genomic, nucleic acids, of a biological particle may be Cas proteins, e.g., Cas 9 protein.

The provided partition, including the biological particle, may also include a plurality of nucleic acid barcode molecules. The plurality of nucleic acid barcode molecules may include a partition-specific barcode sequence and a capture sequence. A first nucleic acid barcode molecule of the plurality of nucleic acid molecules may have a capture sequence that is complementary to a nucleotide sequence of a splint oligonucleotide, which may also be present in the provided partition. In some embodiments, the plurality of nucleic acid barcode molecules may further include second, third, fourth, etc., nucleic acid barcode molecules. Second, third, fourth, etc., nucleic acid barcode molecules are discussed later herein and may be useful for determining presence or levels of analytes of the biological particle, e.g., mRNA or protein analytes expressed from the exogenous insert and/or endogenous nucleic acid sequences of the biological particle. In addition to including a partition-specific barcode sequence and a capture sequence, the first nucleic acid barcode molecule may include one or more functional sequences, such as a unique molecule identifier (UMI) sequence, a sequencer attachment sequence, a sequencing primer sequence, an amplification primer sequence, or complements thereof.

The provided partition, in addition to including the biological particle and the plurality of nucleic acid barcode molecules, may include a first insert primer and a splint oligonucleotide. The first insert primer may include, from 5' to 3', a splinting sequence and a sequence complementary to a first sequence of the exogenous insert. The first sequence of the exogenous insert, to which the first sequence of the exogenous insert may be complementary, may be a sequence of the exogenous insert that is within about 15 to 150 nucleotides, about 15 to 125 nucleotides, about 15 to 100 nucleotides, about 15 to 75 nucleotides, about 15 to 50 nucleotides, about 20 to 150 nucleotides, about 20 to 125 nucleotides, about 20 to 100 nucleotides, about 20 to 75 nucleotides, about 20 to 50 nucleotides, about 50 to 150 nucleotides, about 50 to 125 nucleotides, about 50 to 100 nucleotides or about 50 to 75 nucleotides from 5' or 3' end of the exogenous insert, e.g., junction between the exogenous insert and the first endogenous flanking sequence. The splint oligonucleotide may include a sequence complementary to: (i) the capture sequence of the first nucleic acid barcode molecule and (ii) the splinting sequence of the first insert primer, as discussed earlier herein above.

In the method, the provided partition may be subjected to conditions. The conditions may be sufficient to couple the first nucleic acid barcode molecule to the first insert primer. In some instances, the conditions sufficient to couple the first nucleic acid barcode molecule to the first insert primer may be conditions sufficient to cause the splint oligonucleotide to hybridize to (i) the first insert primer and (ii) the first nucleic acid barcode molecule. In such instances, the hybidization may be via complementary base pairing, e.g., complementary base pairing of the splint oligonucleotide to (i) the first insert primer and (ii) the first nucleic acid barcode molecule. Further yet, (i) the splinting sequence of the first insert primer may hybridize, e.g., via complementary base pairing, to the splinting oligonucleotide's sequence complementary to the first insert primer's splinting sequence; and (ii) the capture sequence of the first nucleic acid barcode molecule may hybridize, e.g., via complementary base pairing, to the splint oligonucleotide's sequence complementary to the first nucleic acid barcode molecule's capture sequence.

The coupling of the first nucleic acid barcode molecule to the first insert primer, e.g., after their hybridization to the splint oligonucleotide, may be by ligation or by chemical conjugation. In instances in which the first nucleic acid barcode molecule is coupled to the first insert primer by ligation, the ligation may be mediated by an enzyme, e.g., enzyme capable of nick repair such as ligases and polymerases. Non-limiting examples of ligases and polymerases include DNA polymerases, reverse transcriptases and DNA ligases such as T4 DNA ligase, T7 DNA ligase, HiFi Taq DNA ligase and SplintR Ligase. In instances in which the first nucleic acid barcode molecule is coupled to the first insert primer by chemical conjugation, the conjugation may be by click reaction chemistry, such as a Methyltetrazine-PEG5-NHS Ester reaction, a TCO-PEG4-NHS Ester reaction, or the like. Commercially available kits, such as those from Thunderlink and Abcam may be used chemically conjugate the first nucleic acid barcode molecule to the first insert primer.

The conditions to which the provided partition may also be sufficient to hybridize the barcoded first insert primer, generated from coupling of the first nucleic acid barcode molecule to the first insert primer, to the first sequence of the exogenous insert. The hybridization of the first insert primer to the first sequence of the exogenous insert may be via complementary base pairing.

In some embodiments, embodiments in which the heterologous nucleic acid molecule is a dsDNA molecule the provided partition may further be subjected to conditions sufficient to denature the dsDNA molecule.

By way of example, conditions sufficient to couple the first nucleic acid barcode molecule to the first insert primer to generate a barcoded first insert primer may include conditions in which the partition is held at a temperature of 15° C. to 40° C. e.g., 15° C., 17° C., 19° C., 21° C., 23° C., 25° C., 27° C., 29° C. 31° C., 33° C. 35° C., 37° C., 39° C. or 40° C. for a period of time of about 5 to 20 minutes, e.g., 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes or 20 minutes. These conditions of 15° C. to 40° C., e.g., about 25° C., over a period of time of 5 to 20 minutes, e.g., about 10 minutes, may be sufficient for a ligase or polymerase, e.g., reverse transcriptase, to couple the first nucleic acid barcode molecule to the first insert primer to generate a barcoded first insert primer and to hybridize the barcoded first insert primer to the first sequence of the exogenous insert of the heterologous nucleic acid molecule. In embodiments in which the heterologous nucleic acid molecule is a dsDNA molecule, conditions sufficient to denature the dsDNA molecule may include holding the partition at a temperature of about 90° C. to about 100° C., e.g., 90° C., 91° C., 92° C., 93° C., 94° C., 95° C., 963° C., 97° C., 98° C., 99° C. or 100° C. following the coupling of the first nucleic acid barcode molecule to the first insert primer to generate the barcoded first insert primer.

In the method, a first barcoded nucleic acid molecule may be generated. The first barcoded nucleic acid molecule may include: (i) the partition-specific barcode sequence, or a reverse complement thereof, and (ii) a first endogenous flanking sequence of the endogenous genomic flanking sequences, or a reverse complement thereof. The first barcoded nucleic acid molecule may be generated from the barcoded first insert primer by extending the barcoded first insert primer, hybridized to the first sequence of the exogenous insert, into the first endogenous flanking sequence. The extension of the barcoded first insert primer into the first endogenous flanking sequence may be performed by a polymerase. The polymerase may be a high fidelity polymerse and/or hot start polymerase. Non-limiting examples of such polymerases include Q5@ Hot Start High-Fidelity DNA Polymerase, OneTaq® Hot Start DNA Polymerase, Phusion High Fidelity (Thermo), High Fidelity Polymerase (Jena Biosciences) and Q5® High-Fidelity DNA Polymerase (NEB). In some instances, multiple copies of the first barcoded nucleic acid molecules may be generated. Multiple copies of the first barcoded nucleic acid molecule may be generated via multiple cycles of extending each of a first, then a second, then a third, etc., barcoded first insert primer, its having been hybridized to the first sequence of the exogenous insert, into the first endogenous flanking sequence flanking the insert.

The first barcoded nucleic acid molecules, having been generated by extension of the barcoded first insert primer into the first endogenous flanking sequence, may be generated in the provided partition. The first barcoded nucleic acid molecules may, alternatively, be generated in bulk. The first barcoded nucleic acid molecules may be generated in bulk by: (i) hybridization of barcoded first insert primers to first sequences of the exogenous insert in the provided partitions and (ii) pooling, from a plurality of partitions, the barcoded first insert primers hybridized to the first sequence of the exogenous inserts of the heterologous nucleic acid molecules.

Once the first barcoded nucleic acid molecule is generated, it may be subjected to optional, additional processing steps. One such optional, additional processing step is a fragmenting step. In some embodiments, the fragmenting step may occur while the first barcoded nucleic acid molecule is hybridized to the first endogenous flanking sequence. In other embodiments, the fragmenting step may occur after a single-stranded first barcoded nucleic acid molecule, e.g., first barcoded nucleic acid molecule no longer hybridized to the first endogenous flanking sequence, is subjected to a second strand synthesis reaction, e.g., using a random primer, to produce a double stranded (ds) derivative of the first barcoded for subjecting to the fragmenting step. The fragmenting step, in either embodiment, may be performed by an RE, e.g., type I or II RE, or a fragmenting enzyme. REs, REs recognition sites and the relationship of the RE's recognition and cleavage sites have been described earlier herein. The fragmenting step may provide a barcoded fragment of a first barcoded nucleic acid molecule.

Further or alternative, optional, processing steps include steps that may attach, e.g., via ligation, a first adaptor to any of the barcoded first nucleic acid molecule, the ds derivative of the barcoded first nucleic acid molecule, the barcoded fragment of the first barcoded nucleic acid molecule, or any derivative or amplicon thereof. Attachment of the first adaptor may be performed to produce an adapted barcoded product. The first adaptor may include a reverse primer binding site. In some embodiments, the adapted barcoded product may be amplified using a first primer that hybridizes to the reverse primer binding site. In other embodiments, the adapted barcoded product may be amplified utilizing the first primer that hybridizes to the reverse primer binding site and a second primer that hybridizes to a forward primer binding site. The forward primer binding site may be a sequence, or complement thereof, incorporated in the first nucleic acid barcode molecule.

In the any of the methods provided herein, from the first barcoded nucleic acid molecule or any derivative (e.g, ds derivative, barcoded fragment, adapted barcoded product or amplified adapted barcoded product) or amplicon thereof, a sequence of the first endogenous flanking sequence may be determined. The determination of the sequence of the first endogenous flanking sequence, or any other nucleic acid molecule described herein, may be performed by any of a variety of approaches, systems, or techniques, including next-generation sequencing (NGS) methods. Sequencing may be performed using nucleic acid amplification, polymerase chain reaction (PCR) (e.g., digital PCR and droplet digital PCR (ddPCR), quantitative PCR, real time PCR, multiplex PCR. PCR-based singleplex methods, emulsion PCR), and/or isothermal amplification. Non-limiting examples of nucleic acid sequencing methods include Maxam-Gilbert sequencing and chain-termination methods, de novo sequencing methods including shotgun sequencing and bridge PCR, next-generation methods including Polony sequencing, 454 pyrosequencing, Illumina sequencing. SOLiD™ sequencing. Ion Torrent semiconductor sequencing. HeliScope single molecule sequencing, nanopore sequencing (Oxford Nanopore) and SMRT® sequencing.

Other examples of methods for determining the sequence of the first endogenous flanking sequence of the first barcoded nucleic acid molecule, or any derivative (e.g. ds derivative, barcoded fragment thereof, adapted barcoded product or amplified adapted barcoded product) or amplicon thereof include, but are not limited to, DNA hybridization methods, restriction enzyme digestion methods, Sanger sequencing methods, ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing. Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, Solexa Genome Analyzer sequencing. MS-PET sequencing, whole transcriptome sequencing, and any combinations thereof.

The determined sequence of the first endogenous flanking sequence may map the location at which the exogenous insert is inserted in the biological particle's endogenous sequences. The determined sequence of the first endogenous flanking sequence may additionally, or alternatively, characterize the biological particle as including the exogenous insert at a particular location in its endogenous sequences.

In some embodiments, mapping the location in which the exogenous insert is inserted in the biological particle's endogenous sequences may identify the location of its insertion site as capable of dysregulating expression of one or more endogenous genes of the biological particle. Examples of insertion site locations that may dysregulate expression of one or more of the biological particle's endogenous genes include those that: (i) activate an endogenous gene, e.g., due to their being adjacent to an oncogene, (ii) interrupt an endogenous gene or (iii) silence an endogenous gene. In instances in which the biological particle includes the exogenous insert and the biological particle is for administration to a subject, identifying the location of the insertion site as being capable of dysregulating expression of one or more of the biological particle's endogenous genes may determine that the biological particle is unsuitable for administration.

In other embodiments, embodiments in which a gene editing protein with sequence-specific integration characteristics, e.g., a Cas protein, has been employed to introduce the exogenous insert in the biological particle's endogenous nucleic acids, mapping the insertion site of the exogenous insert may characterize the biological particle as having the exogenous insert at a location that is on- or off-target. In these embodiments, the cell may be characterized as having on-target insertion of the exogenous insert if the first endogenous flanking sequence reflects the sequence-specific integration characteristics of the gene editing protein. Also in these embodiments, the cell is characterized as comprising off-target insertion of the exogenous insert if the first endogenous flanking sequence does not reflect the sequence-specific integration characteristics of the gene editing protein.

In any of the methods provided herein above, a sequence of a second endogenous flanking sequence of the endogenous flanking sequences may also be determined. The sequence of the second endogenous flanking sequence may be determined to confirm the location of the insertion site of the exogenous insert, e.g. determined from the first endogenous flanking sequence's nucleic acid sequence. The sequence of the second endogenous flanking sequence may be determined to ascertain whether any disruptions, e.g., rearrangements or deletions, had been introduced in the biological particle's endogenous nucleic acids as a result of insertion of the exogenous insert in the biological particle's endogenous nucleic acids.

The sequence of the second endogenous flanking sequence may be determined from a further barcoded nucleic acid molecule, or a derivative (e.g. ds derivative, barcoded fragment thereof, adapted barcoded product or amplified adapted barcoded product) or amplicon thereof. The further barcoded nucleic acid molecule may include: (i) the partition-specific barcode sequence or a reverse complement thereof and (ii) a second endogenous flanking sequence of the endogenous genomic flanking sequences or a reverse complement thereof. The further barcoded nucleic acid molecule may be generated from a second insert primer having been included in the provided partition, wherein the second insert primer may have, from 5' to 3', a splinting sequence (which may be the same as or different from the splinting sequence of the first insert primer) and a sequence complementary to a second sequence of the exogenous insert; the second sequence of the exogenous insert being from the opposite e.g. 5' or 3', end of the first sequence of the exogenous insert. In instances in which the splinting sequence of the second insert primer differs from that of the first insert primer, the provided partition may include a second splint oligonucleotide having a sequence complementary to the capture sequence of a first nucleic acid barcode molecule of the plurality of nucleic acid barcode molecules and a sequence complementary to the splinting sequence of the second insert primer.

In any of the methods provided herein, the biological particle may further be characterized by determining expression of one or more analytes by the biological particle. The one or more analytes may nucleic acid, e.g., mRNA, or peptide analytes. The one or more analytes may be analytes encoded by the exogenous insert or may be analytes encoded by the biological particle's endogenous nucleic acids.

In some embodiments, the one or more analytes may be or include an mRNA analyte. In these embodiments, expression of an mRNA analyte may be determined by generation of a second barcoded nucleic acid molecule. A second barcoded nucleic acid molecule may include: (i) the partition-specific barcode sequence, or a reverse complement thereof; and (ii) at least a portion of a nucleic acid sequence of the mRNA analyte, or a reverse complement thereof. The second barcoded nucleic acid molecule, e.g., including the partition-specific barcode sequence (or reverse complement thereof) and the at least a portion of the nucleic acid sequence or the mRNA analyte (or reverse complement thereof), may be generated from the mRNA analyte and a second nucleic acid barcode molecule of the plurality of nucleic acid barcode molecules included in the provided partition. The second nucleic acid barcode molecule may include the partition-specific barcode sequence and a second capture sequence. In some aspects, the second capture sequence may be configured to couple to the mRNA analyte. The second capture sequence, configured to couple to the mRNA analyte, may include a polyT sequence, a random sequence, or a sequence complementary to a gene-specific sequence of the mRNA analyte. In other aspects, the second capture sequence may be configured to couple to non-templated nucleotides appended to a cDNA reverse transcribed, by a reverse transcriptase having terminal transferase activity, from an mRNA analyte of the biological particle. In instances of these aspects, the mRNA analyte may be reversed transcribed to the cDNA using a polyT primer, a primer of random sequence, or a primer with sequence complementary to a gene-specific sequence as discussed above. During reverse transcription, the reverse transcriptase, via its terminal transferase activity, may append one or more non-templated nucleotides. e.g., cytosines (e.g., CCC), to the cDNA. If the non-templated nucleotides appended to the cDNA are cytosines, the second capture sequence of the second nucleic acid barcode molecule may include one or more guanines (e.g., GGG). The second capture sequence of the second nucleic acid barcode molecule may couple to the non-templated nucleotides appended to the cDNA reverse transcribed from the mRNA analyte, and the reverse transcriptase may extend reverse transcription of the cDNA into the second nucleic acid barcode molecule to generate the second barcoded nucleic molecule. The second nucleic acid barcode molecule, in addition to the partition-specific barcode sequence and second capture sequence, may further include one or more functional sequences, such as a unique molecule identifier (UMI), sequencer attachment sequence, sequencing primer sequence, amplification primer sequence, template switch oligonucleotide (TSO) sequence, or the complements thereof.

Additionally or alternatively, the one or more analytes may be or include a peptide, polypeptide, protein, or other (e.g., CRISPR/gRNA) analyte. In these embodiments, expression of the peptide or other analyte may be determined utilizing a labeling agent that binds the analyte. In some instances, the labeling agent may be operatively coupled to a first reporter oligonucleotide. The first reporter oligonucleotide operatively coupled to the labeling agent may include a first reporter barcode sequence and a capture handle sequence. The first reporter barcode sequence of the reporter oligonucleotide may identify the labeling agent to which it is operatively coupled. The capture handle sequence of the reporter oligonucleotide may be complementary to a third capture sequence of a third nucleic acid barcode molecule of the plurality of nucleic acid barcode molecules. The reporter oligonucleotide may, optionally, additionally include functional sequences such as a UMI or primer binding sequence. In instances in which the labeling agent is operatively coupled to a reporter oligonucleotide, a third barcoded nucleic acid molecule may be generated that includes: (i) the partition-specific barcode sequence, or a reverse complement thereof; and (ii) the third reporter barcode sequence, or a reverse complement thereof. The third barcoded nucleic acid molecule may determine expression of the peptide, polypeptide, protein, or other (e.g., CRISPR/gRNA) analyte.

Additionally or alternatively, the labeling agent may include a fluorescent molecule. In such instances, expression of a peptide analyte may be determined by identification of biological particles having bound the labeling agent by fluorescence activated cell sorting (FACS). Non-limiting examples of fluorescent molecules that may be included with the labeling agent for detecting peptide analytes include: Alexa Fluor 350, DyLight 405, Alexa Fluor 405, Pacific Blue, Alexa Fluor 405, Alexa Fluor 430, Alexa Fluor 488, fluorescein isothiocyanate (FITC), Alexa Fluor 532, Alexa Fluor 546, DyLight 550, phycocrythrin (PE), allophycocyanin (APC), Alexa Fluor 555, Alexa Fluor 561, Alexa Fluor 568, Alexa Fluor 594, Alexa Fluor 610, Alexa Fluor 633, Alexa Fluor 635, Alexa Fluor 647, DyLight 650, peridinin chlorophyll protein (PerCP), Alexa Fluor 660, Alexa Fluor 680, Alexa Fluor 700, Alexa Fluor 750, Alexa Fluor 790, Coumarin, borondipyrromethene (BODIPY), Pacific Green, Oregon Green, cyanine (Cy)3, Cy5, Pacific Orange, PE-Cy7, PerCP-Cy5.5, Tetramethylrhodaminie (TRITC), Texas Red, StarBright Violet 440, StarBright Violet 515, StarBright 610, StarBright Violet 670 or StarBright Blue 700.

The detecting and/or identification of a biological particle as having bound, or become associated with, the labeling agent having the fluorescent molecule, by FACS, may select the biological particle for inclusion in a provided partition. In some instances, the labeling agent having the fluorescent molecule may bind a peptide analyte encoded by the exogenous insert. In such instances biological particles expressing the peptide analyte encoded by the exogenous insert may be selected, by FACs, prior to their inclusion in a partition, e.g., a provided partition. It will be understood that in some embodiments the labeling agent may be operatively coupled to a reporter oligonucleotide and additionally include a fluorescent molecule.

In any of the methods provided herein, determining expression of any one or more analytes of the biological particle may be a determination that the one or more analytes is expressed. In any of the methods provided herein, determining expression of any one or more analytes of the biological particle may be a determination of level of expression of the one or more analytes. Level of expression of the one or more analytes may be determined, in embodiments in which analyte detection is via generation of barcoded nucleic acid molecules, by quantitating the generated barcoded nucleic acid molecules associated with the one or more analytes. By way of example, the quantitating the generated barcoded nucleic acid molecules may be by counting/quantiting UMI sequences (UMI sequences that may be included in a reporter oligonucleotide or a nucleic acid barcode molecule of the plurality of nucleic acid barcode molecules), of the generated barcoded nucleic acid molecules associated with the analyte. Level of expression of analytes, in embodiments in which the analyte may be detected via FACS, may be by detecting level of fluorescence associated the analyte having bound to or been associated with the biological particle.

In instances in which the biological particle is further characterized by determining expression of one or more analytes, e.g., nucleic acid or peptide analytes, the expression may be useful to characterize effects of the exogenous insert's insertion site on expression of the exogenous insert and/or, more generally, on its global gene expression patterns.

In instances in which the biological particle is further characterized by determining expression of one or more peptide analytes. e.g., employing labeling agents, the labeling agents may be added to the provided partition, or the labeling agents may be contacted with the biological particle in a reaction mixture prior to the biological particle's inclusion in the provided partition. The labeling agents may be those described earlier herein, operatively coupled to reporter oligonucleotides and/or including fluorescent molecules. The labeling agents may further, and more generally, be configured to bind or otherwise couple to one or more surface features of the biological particle and be useful to characterize of the biological particle, e.g., characterize the biological particle as being of a particular lineage or activation state. In instances in which the labeling agents are operatively coupled to reporter oligonucleotides, different reporter oligonucleotides may have different adapter sequences, e.g., different primer sequences or primer binding sequences. In instances in which the labeling agents include fluorescent molecules, different fluorescent molecules may have be used for different analytes or surface features or may be used for different categories of analytes or surface features. In some embodiments, the labeling agents may be configured such that they are coupled to a solid support, e.g., streptavidin, avidin, deglycosylated avidin, traptavidin, tamavidin, xenavidin, or bradavidin. In these embodiments, the labeling agents may be biotinylated and coupled to the solid support, e.g., streptavidin, avidin, deglycosylated avidin, traptavidin, tamavidin, xenavidin, or bradavidin.

A reaction mixture may also include a control reagent. A control reagent may include a protein or peptide to which the biological particle would not be expected to bind, e.g., a serum albumin, and can be operatively coupled to a reporter oligonucleotide or include a fluorescent molecule, e.g., fluorescent molecule that emits a different fluorescent signal than a fluorescent molecule included with a labeling agent. In some embodiments, embodiments in which the labeling agents are configured to be coupled to a solid support, the control reagent may be the solid support, e.g., streptavidin, avidin, deglycosylated avidin, traptavidin, tamavidin, xenavidin, or bradavidin, or may be a biotinylated solid support, e.g., streptavidin, avidin, deglycosylated avidin, traptavidin, tamavidin, xenavidin, or bradavidin.

The reaction mixture, or a portion thereof, may be partitioned so as to provide biological particles to the provided partitions.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion or a well. A partition can be a volume wherein diffusion of contents beyond the volume is inhibited. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more beads. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead.

Unique identifiers, such as barcodes, may be injected into the droplets previous to, subsequent to, or concurrently with droplet generation, such as via a bead, as described elsewhere herein.

The methods and systems of the present disclosure may comprise methods and systems for generating one or more partitions such as droplets. The droplets may comprise a plurality of droplets in an emulsion. In some examples, the droplets may comprise droplets in a colloid. In some cases, the emulsion may comprise a microemulsion or a nanoemulsion. In some examples, the droplets may be generated with aid of a microfluidic device and/or by subjecting a mixture of immiscible phases to agitation (e.g., in a container). In some cases, a combination of the mentioned methods may be used for droplet and/or emulsion formation.

The partitions described herein may comprise small volumes, for example, less than about 10 microliters (μL), 5 μL, 1 μL, 10 nanoliters (nL), 5 nL, 1 nL, 900 picoliters (pL), 800 pL, 700 pL, 600 pL, 500 pL, 400 pL, 300 pL, 200 pL, 100 pL, 50 pL, 20 pL, 10 μL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with beads, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Droplets can be formed by creating an emulsion by mixing and/or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

Microfluidic Systems

Microfluidic devices or platforms comprising microfluidic channel networks (e.g., on a chip) can be utilized to generate partitions such as droplets and/or emulsions as described herein. Methods and systems for generating partitions such as droplets, methods of encapsulating biological particles in partitions, methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In some examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as biological particles, in some cases, individual biological particles such as single cells. In some examples, reagents may be encapsulated and/or partitioned (e.g., co-partitioned with biological particles) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, flows can be controlled so as to present a non-Poissonian distribution of single-occupied partitions while providing lower levels of unoccupied partitions (e.g., no more than about 50%, about 25%, or about 10% unoccupied). The above noted ranges of unoccupied partitions can be achieved while still providing any of the single occupancy rates described above.

As will be appreciated, the above-described occupancy rates are also applicable to partitions that include both biological particles and additional reagents, such as beads (e.g., gel beads) carrying nucleic acid barcode molecules (e.g., oligonucleotides).

In some examples, a partition of the plurality of partitions may comprise a single biological particle (e.g., a single cell or a single nucleus of a cell). In some examples, a partition of the plurality of partitions may comprise multiple biological particles. Such partitions may be referred to as multiply occupied partitions, and may comprise, for example, two, three, four or more cells and/or beads (e.g., beads) comprising nucleic acid barcode molecules within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

Microfluidic systems for partitioning are further described in U.S. Patent Application Pub. No. US 2015/0376609, which is hereby incorporated by reference in its entirety.

Figure 15:
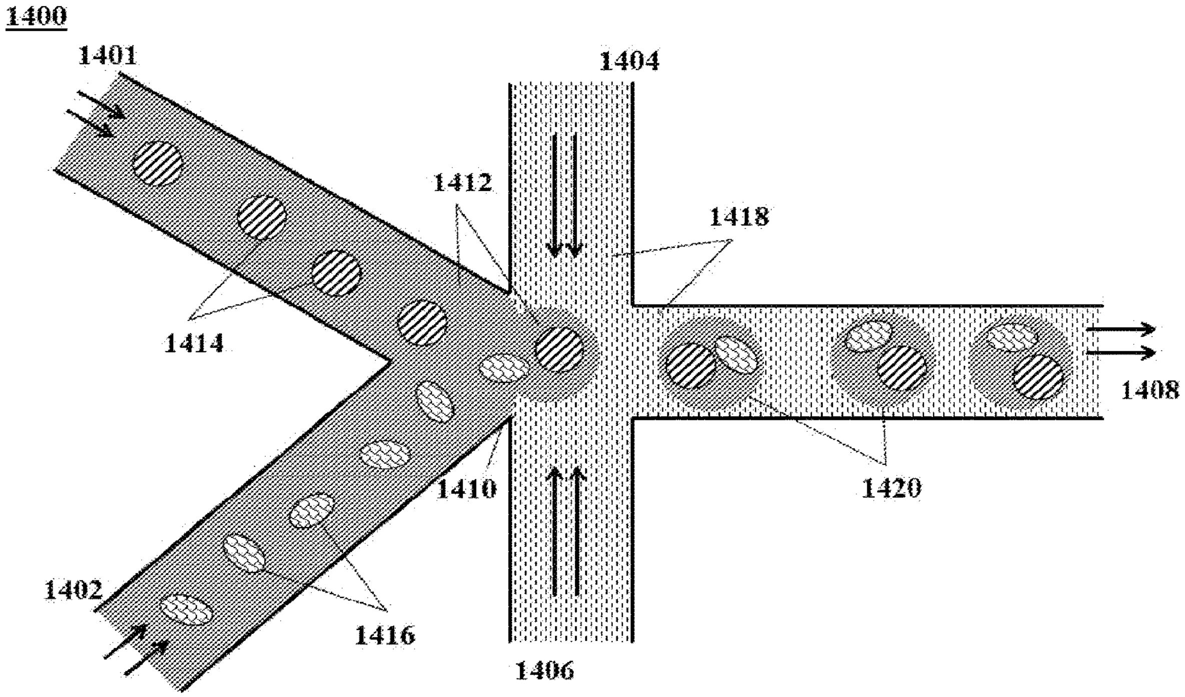
FIG. 15 shows an exemplary microfluidic channel structure for delivering barcode carrying beads to droplets.

FIG. 15 shows an example of a microfluidic channel structure 1400 for delivering barcode carrying beads to droplets. The channel structure 1400 can include channel segments 1401, 1402, 1404, 1406 and 1408 communicating at a channel junction 1410. In operation, the channel segment 1401 may transport an aqueous fluid 1412 that includes a plurality of beads 1414 (e.g., with nucleic acid molecules, e.g., nucleic acid barcode molecules or barcoded oligonucleotides, molecular tags) along the channel segment 1401 into junction 1410. The plurality of beads 1414 may be sourced from a suspension of beads. For example, the channel segment 1401 may be connected to a reservoir comprising an aqueous suspension of beads 1414. The channel segment 1402 may transport the aqueous fluid 1412 that includes a plurality of biological particles 1416 along the channel segment 1402 into junction 1410. The plurality of biological particles 1416 may be sourced from a suspension of biological particles. For example, the channel segment 1402 may be connected to a reservoir comprising an aqueous suspension of biological particles 1416. In some instances, the aqueous fluid 1412 in either the first channel segment 1401 or the second channel segment 1402, or in both segments, can include one or more reagents, as further described below. A second fluid 1418 that is immiscible with the aqueous fluid 1412 (e.g., oil) can be delivered to the junction 1410 from each of channel segments 1404 and 1406. Upon meeting of the aqueous fluid 1412 from each of channel segments 1401 and 1402 and the second fluid 1418 from each of channel segments 1404 and 1406 at the channel junction 1410, the aqueous fluid 1412 can be partitioned as discrete droplets 1420 in the second fluid 1418 and flow away from the junction 1410 along channel segment 1408. The channel segment 1408 may deliver the discrete droplets to an outlet reservoir fluidly coupled to the channel segment 1408, where they may be harvested. As an alternative, the channel segments 1401 and 1402 may meet at another junction upstream of the junction 1410. At such junction, beads and biological particles may form a mixture that is directed along another channel to the junction 1410 to yield droplets 1420. The mixture may provide the beads and biological particles in an alternating fashion, such that, for example, a droplet comprises a single bead and a single biological particle.

Controlled Partitioning

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 2:
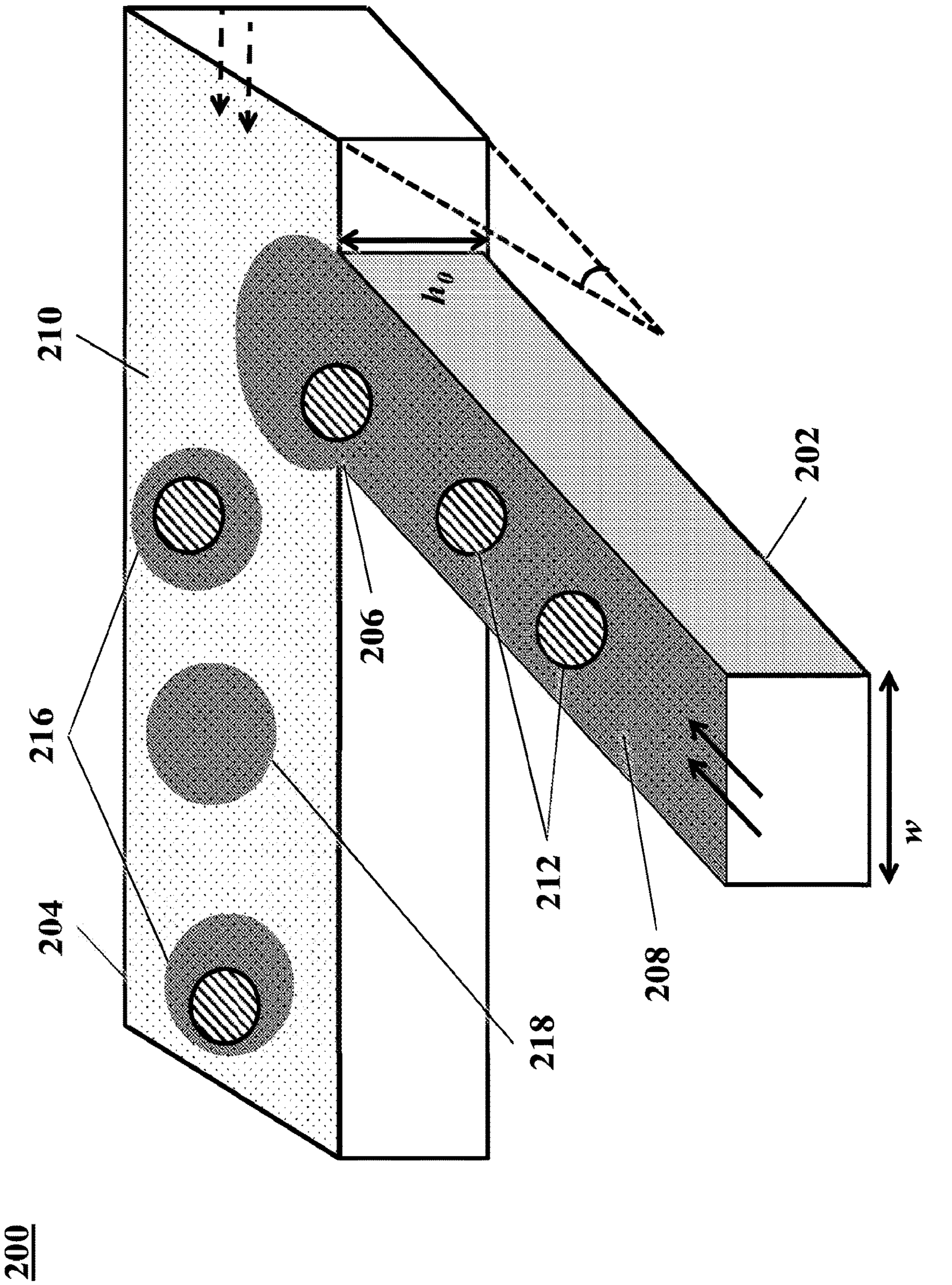
FIG. 2 shows an example of a microfluidic channel structure for the controlled partitioning of beads into discrete droplets.

FIG. 2 shows an example of a microfluidic channel structure for the controlled partitioning of beads into discrete droplets. A channel structure 200 can include a channel segment 202 communicating at a channel junction 206 (or intersection) with a reservoir 204. The reservoir 204 can be a chamber. Any reference to "reservoir." as used herein, can also refer to a "chamber." In operation, an aqueous fluid 208 that includes suspended beads 212 may be transported along the channel segment 202 into the junction 206 to meet a second fluid 210 that is immiscible with the aqueous fluid 208 in the reservoir 204 to create droplets 216, 218 of the aqueous fluid 208 flowing into the reservoir 204. At the junction 206 where the aqueous fluid 208 and the second fluid 210 meet, droplets can form based on factors such as the hydrodynamic forces at the junction 206, flow rates of the two fluids 208, 210, fluid properties, and certain geometric parameters (e.g., w, h0, α, etc.) of the channel structure 200. A plurality of droplets can be collected in the reservoir 204 by continuously injecting the aqueous fluid 208 from the channel segment 202 through the junction 206.

In some instances, the aqueous fluid 208 can have a substantially uniform concentration or frequency of beads 212. The beads 212 can be introduced into the channel segment 202 from a separate channel (not shown in FIG. 2). The frequency of beads 212 in the channel segment 202 may be controlled by controlling the frequency in which the beads 212 are introduced into the channel segment 202 and/or the relative flow rates of the fluids in the channel segment 202 and the separate channel. In some instances, the beads can be introduced into the channel segment 202 from a plurality of different channels, and the frequency controlled accordingly.

In some instances, the aqueous fluid 208 in the channel segment 202 can comprise biological particles. In some instances, the aqueous fluid 208 can have a substantially uniform concentration or frequency of biological particles. As with the beads, the biological particles can be introduced into the channel segment 202 from a separate channel. The frequency or concentration of the biological particles in the aqueous fluid 208 in the channel segment 202 may be controlled by controlling the frequency in which the biological particles are introduced into the channel segment 202 and/or the relative flow rates of the fluids in the channel segment 202 and the separate channel. In some instances, the biological particles can be introduced into the channel segment 202 from a plurality of different channels, and the frequency controlled accordingly. In some instances, a first separate channel can introduce beads and a second separate channel can introduce biological particles into the channel segment 202. The first separate channel introducing the beads may be upstream or downstream of the second separate channel introducing the biological particles.

The second fluid 210 can comprise an oil, such as a fluorinated oil, that includes a fluorosurfactant for stabilizing the resulting droplets, for example, inhibiting subsequent coalescence of the resulting droplets.

In some instances, the second fluid 210 may not be subjected to and/or directed to any flow in or out of the reservoir 204. For example, the second fluid 210 may be substantially stationary in the reservoir 204. In some instances, the second fluid 210 may be subjected to flow within the reservoir 204, but not in or out of the reservoir 204, such as via application of pressure to the reservoir 204 and/or as affected by the incoming flow of the aqueous fluid 208 at the junction 206. Alternatively, the second fluid 210 may be subjected and/or directed to flow in or out of the reservoir 204. For example, the reservoir 204 can be a channel directing the second fluid 210 from upstream to downstream, transporting the generated droplets.

Systems and methods for controlled partitioning are described further in PCT/US2018/047551, which is hereby incorporated by reference in its entirety.

Cell Beads

A cell bead can contain a biological particle (e.g., a cell) or macromolecular constituents (e.g., RNA, DNA, proteins, etc.) of a biological particle. A cell bead may include a single cell or multiple cells, or a derivative of the single cell or multiple cells. For example, after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Cell beads can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli (or reagents).

Suitable polymers or gels may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. The conditions sufficient to polymerize or gel the precursors may comprise any conditions sufficient to polymerize or gel the precursors. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), electromagnetic radiation, mechanical stimuli, or any combination thereof.

In some cases, air knife droplet or aerosol generators may be used to dispense droplets of precursor fluids into gelling solutions in order to form cell beads that include individual biological particles or small groups of biological particles. Likewise, membrane-based encapsulation systems may be used to generate cell beads comprising encapsulated biological particles as described herein. Microfluidic systems of the present disclosure, such as that shown in FIG. 1, may be readily used in encapsulating biological particles (e.g., cells) as described herein. Exemplary methods for encapsulating biological particles (e.g., cells) are also further described in U.S. Patent Application Pub. No. US 2015/0376609 and PCT/US2018/016019, which are hereby incorporated by reference in their entirety. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the bead that includes the entrained biological particles. Examples of polymer precursor/initiator pairs include those described in U.S. Patent Application Publication No. 2014/0378345, which is entirely incorporated herein by reference for all purposes.

In some cases, encapsulated biological particles can be selectively releasable from the cell bead, such as through passage of time or upon application of a particular stimulus, that degrades the bead sufficiently to allow the biological particles (e.g., cell), or its other contents to be released from the bead, such as into a partition (e.g., droplet). Exemplary stimuli suitable for degradation of the bead are described in U.S. Patent Application Publication No. 2014/0378345, which is entirely incorporated herein by reference for all purposes.

The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel.

The polymer or gel may be functionalized to bind to targeted analytes, such as nucleic acids, proteins, carbohydrates, lipids or other analytes. The polymer or gel may be functionalized to couple or link to a plurality of capture agents. The plurality of capture agents may, e.g., covalently or non-covalently, couple or link to the backbone of the polymer. See, e.g., U.S. Pat. No. 10,590,244, which is incorporated by reference in its entirety, for exemplary cell bead functionalization strategies. In an embodiment, a first capture agent of a plurality of capture agents may be a polypeptide or aptamer that (i) couples or links to the backbone of the polymer, and (ii) binds a specific analyte (e.g., antibody or antigen-binding fragment thereof) secreted by the cell, e.g., B cell. By way of example, a first capture agent of a plurality of capture agents may be a polypeptide, e.g., antibody, or aptamer that couples/links to the backbone of the polymer and binds to a secreted antibody, e.g., at its Fc region. It will be understood that, in some embodiments, the first capture agent of the plurality of capture agents may, rather than couple/link to the backbone of the polymer of the gel matrix, embed in/couple to the cell membrane. In these embodiments, the first capture agent, e.g., polypeptide or aptamer, may (i) embed in the membrane of the cell and/or bind to a cell surface protein and (ii) bind the specific analyte, e.g., antibody or antigen-binding fragment thereof, thereby tethering the secreted analyte, e.g., antibody, to the cell.

The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The encapsulation of biological particles may constitute the partitioning of the biological particles into which other reagents are co-partitioned. Alternatively or in addition, encapsulated biological particles may be readily deposited into other partitions (e.g., droplets) as described above.

Beads

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

The solid support may be a bead. A solid support, e.g., a bead, may be porous, non-porous, hollow, solid, semi-solid, and/or a combination thereof. Beads may be solid, semi-solid, semi-fluidic, fluidic, and/or a combination thereof. In some instances, a solid support, e.g., a bead, may be at least partially dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support. e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual biological particle to the particular partition. Barcodes may be delivered, for example on a nucleic acid molecule (e.g., via a nucleic acid barcode molecule), to a partition via any suitable mechanism. Nucleic acid barcode molecules can be delivered to a partition via a bead. Beads are described in further detail below.

In some cases, nucleic acid barcode molecules can be initially associated with the bead and then released from the bead. Release of the nucleic acid barcode molecules can be passive (e.g., by diffusion out of the bead). In addition or alternatively, release from the bead can be upon application of a stimulus which allows the nucleic acid barcode molecules to dissociate or to be released from the bead. Such stimulus may disrupt the bead, an interaction that couples the nucleic acid barcode molecules to or within the bead, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

Methods and systems for partitioning barcode carrying beads into droplets are provided herein, and in in US. Patent Publication Nos. 2019/0367997 and 2019/0064173, and International Application No. PCT/US20/17785, each of which is herein entirely incorporated by reference for all purposes.

A bead may be porous, non-porous, solid, semi-solid, semi-fluidic, fluidic, and/or a combination thereof. In some instances, a bead may be dissolvable, disruptable, and/or degradable. Degradable beads, as well as methods for degrading beads, are described in PCT/US2014/044398, which is hereby incorporated by reference in its entirety. In some cases, any combination of stimuli, e.g., stimuli described in PCT/US2014/044398 and US Patent Application Pub. No. 2015/0376609, hereby incorporated by reference in its entirety, may trigger degradation of a bead. For example, a change in pH may enable a chemical agent (e.g., DTT) to become an effective reducing agent.

In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm. 5 μm, 10 μm, 20 μm, 30 μm. 40 μm, 50 μm, 60 μm, 70 μm, 80 μm, 90 μm, 100 μm. 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. See, e.g., PCT/US2014/044398, which is hereby incorporated by reference in its entirety. Beads may also be formed from materials other than polymers, including lipids, micelles, ceramics, glass-ceramics, material composites, metals, other inorganic materials, and others.

In some cases, the bead may comprise covalent or ionic bonds between polymeric precursors (e.g., monomers, oligomers, linear polymers), nucleic acid barcode molecules (e.g., oligonucleotides), primers, and other entities. In some cases, the covalent bonds can be carbon-carbon bonds, thioether bonds, or carbon-heteroatom bonds.

In some cases, a plurality of nucleic acid barcode molecules may be attached to a bead. The nucleic acid barcode molecules may be attached directly or indirectly to the bead. In some cases, the nucleic acid barcode molecules may be covalently linked to the bead. In some cases, the nucleic acid barcode molecules are covalently linked to the bead via a linker. In some cases, the linker is a degradable linker. In some cases, the linker comprises a labile bond configured to release said nucleic acid barcode molecule of said plurality of nucleic acid barcode molecules. In some cases, the labile bond comprises a disulfide linkage.

Activation of disulfide linkages within a bead can be controlled such that only a small number of disulfide linkages are activated. Methods of controlling activation of disulfide linkages within a bead are described in PCT/US2014/044398, which is hereby incorporated by reference in its entirety.

In some cases, a bead may comprise an acrydite moiety, which in certain aspects may be used to attach one or more nucleic acid barcode molecules (e.g., barcode sequence, nucleic acid barcode molecule, barcoded oligonucleotide, primer, or other oligonucleotide) to the bead. Acrydite moieties, as well as their uses in attaching nucleic acid molecules to beads, are described in PCT/US2014/044398, which is hereby incorporated by reference in its entirety.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule, e.g., a nucleic acid barcode molecule described herein.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. Exemplary precursors comprising functional groups are described in PCT/US2014/044398, which is hereby incorporated by reference in its entirety.

Other non-limiting examples of labile bonds that may be coupled to a precursor or bead are described in PCT/US2014/044398, which is hereby incorporated by reference in its entirety. A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Sec, e.g., PCT/US2014/044398, which is hereby incorporated by reference in its entirety. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Alternatively or in addition, species may be partitioned in a partition (e.g., droplet) during or subsequent to partition formation. Such species may include, without limitation, the abovementioned species that may also be encapsulated in a bead.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

Any suitable number of molecular tag molecules (e.g., primer, barcoded oligonucleotide) can be associated with a bead such that, upon release from the bead, the molecular tag molecules (e.g., primer. e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Nucleic Acid Barcode Molecules

A nucleic acid barcode molecule may contain one or more barcode sequences. A plurality of nucleic acid barcode molecules may be coupled to a bead. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

Nucleic acid barcode molecules can comprise one or more functional sequences for coupling to an analyte or analyte tag such as a reporter oligonucleotide. Such functional sequences can include, e.g., a template switch oligonucleotide (TSO) sequence, a primer sequence (e.g., a poly T sequence, or a nucleic acid primer sequence complementary to a target nucleic acid sequence and/or for amplifying a target nucleic acid sequence, a random primer, and a primer sequence for messenger RNA).

In some cases, the nucleic acid barcode molecule can further comprise a unique molecular identifier (UMI). In some cases, the nucleic acid barcode molecule can comprise one or more functional sequences, for example, for attachment to a sequencing flow cell, such as, for example, a P5 sequence (or a portion thereof) for Illumina® sequencing. In some cases, the nucleic acid barcode molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise an R1 primer sequence for Illumina sequencing. In some cases, the nucleic acid molecule can comprise an R2 primer sequence for Illumina sequencing. In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof.

Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 3:
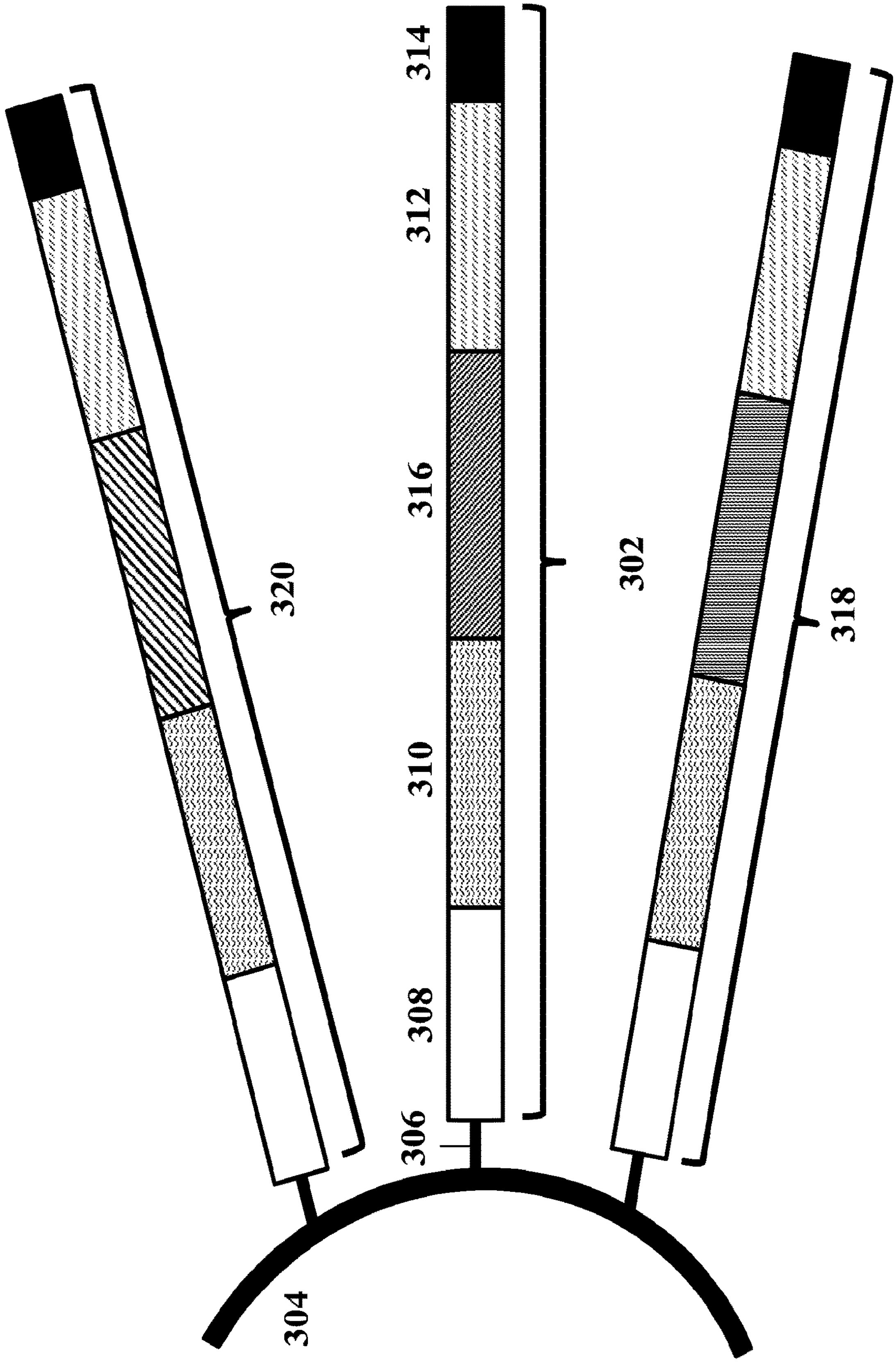
FIG. 3 illustrates an example of a barcode carrying bead.

FIG. 3 illustrates an example of a barcode carrying bead. A nucleic acid barcode molecule 302 can be coupled to a bead 304 by a releasable linkage 306, such as, for example, a disulfide linker. The same bead 304 may be coupled (e.g., via releasable linkage) to one or more other nucleic acid barcode molecules 318, 320. The nucleic acid barcode molecule 302 may be or comprise a barcode. As noted elsewhere herein, the structure of the barcode may comprise a number of sequence elements. The nucleic acid barcode molecule 302 may comprise a functional sequence 308 that may be used in subsequent processing. For example, the functional sequence 308 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid barcode molecule 302 may comprise a barcode sequence 310 for use in barcoding the sample (e.g., DNA, RNA, protein, etc.). In some cases, the barcode sequence 310 can be bead-specific such that the barcode sequence 310 is common to all nucleic acid barcode molecules (e.g., including nucleic acid barcode molecule 302) coupled to the same bead 304. Alternatively or in addition, the barcode sequence 310 can be partition-specific such that the barcode sequence 310 is common to all nucleic acid barcode molecules coupled to one or more beads that are partitioned into the same partition. The nucleic acid barcode molecule 302 may comprise sequence 312 complementary to an analyte of interest. e.g., a priming sequence. Sequence 312 can be a poly-T sequence complementary to a poly-A tail of an mRNA analyte, a targeted priming sequence, and/or a random priming sequence. The nucleic acid barcode molecule 302 may comprise an anchoring sequence 314 to ensure that the specific priming sequence 312 hybridizes at the sequence end (e.g., of the mRNA). For example, the anchoring sequence 314 can include a random short sequence of nucleotides, such as a 1-mer, 2-mer. 3-mer or longer sequence, which can ensure that a poly-T segment is more likely to hybridize at the sequence end of the poly-A tail of the mRNA.

The nucleic acid barcode molecule 302 may comprise a unique molecular identifying sequence 316 (e.g., unique molecular identifier (UMI). In some cases, the unique molecular identifying sequence 316 may comprise from about 5 to about 8 nucleotides. Alternatively, the unique molecular identifying sequence 316 may compress less than about 5 or more than about 8 nucleotides. The unique molecular identifying sequence 316 may be a unique sequence that varies across individual nucleic acid barcode molecules (e.g., 302, 318, 320, etc.) coupled to a single bead (e.g., bead 304). In some cases, the unique molecular identifying sequence 316 may be a random sequence (e.g., such as a random N-mer sequence). For example, the UMI may provide a unique identifier of the starting analyte (e.g., mRNA) molecule that was captured, in order to allow quantitation of the number of original expressed RNA molecules. As will be appreciated, although FIG. 3 shows three nucleic acid barcode molecules 302, 318, 320 coupled to the surface of the bead 304, an individual bead may be coupled to any number of individual nucleic acid barcode molecules, for example, from one to tens to hundreds of thousands, millions, or even a billion of individual nucleic acid barcode molecules. The respective barcodes for the individual nucleic acid barcode molecules can comprise both common sequence segments or relatively common sequence segments (e.g., 308, 310, 312, etc.) and variable or unique sequence segments (e.g., 316) between different individual nucleic acid barcode molecules coupled to the same bead.

In operation, a biological particle (e.g., cell, DNA. RNA, etc.) can be co-partitioned along with a barcode bearing bead 304. The nucleic acid barcode molecules 302, 318, 320 can be released from the bead 304 in the partition. By way of example, in the context of analyzing sample RNA, the poly-T segment (e.g., 312) of one of the released nucleic acid barcode molecules (e.g., 302) can hybridize to the poly-A tail of a mRNA molecule. Reverse transcription may result in a cDNA transcript of the mRNA, but which transcript includes each of the sequence segments 308, 310, 316 of the nucleic acid barcode molecule 302. Because the nucleic acid barcode molecule 302 comprises an anchoring sequence 314, it will more likely hybridize to and prime reverse transcription at the sequence end of the poly-A tail of the mRNA. cDNA transcripts of the individual mRNA molecules from any given partition may include a common barcode sequence segment 310. However, the transcripts made from the different mRNA molecules within a given partition may vary at the unique molecular identifying sequence 312 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid barcode molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where analytes from the sample are captured by the nucleic acid barcode molecules in a partition (e.g., by hybridization), captured analytes from various partitions may be collected, pooled, and subjected to further processing (e.g., reverse transcription, adapter attachment, amplification, clean up, sequencing). For example, in cases wherein the nucleic acid molecules from the sample remain attached to the bead, the beads from various partitions may be collected, pooled, and subjected to further processing (e.g., reverse transcription, adapter attachment, amplification, clean up, sequencing). In other instances, one or more of the processing methods, e.g., reverse transcription, may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, an biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead.

In some instances, a capture sequence coupled to a bead (or other support) may be configured to attach to a linker molecule, such as a splint molecule (or splint oligonucleotide), wherein the linker molecule is configured to couple the bead (or other support) to other molecules through the linker molecule, such as to one or more analytes or one or more other linker molecules.

Figure 4:
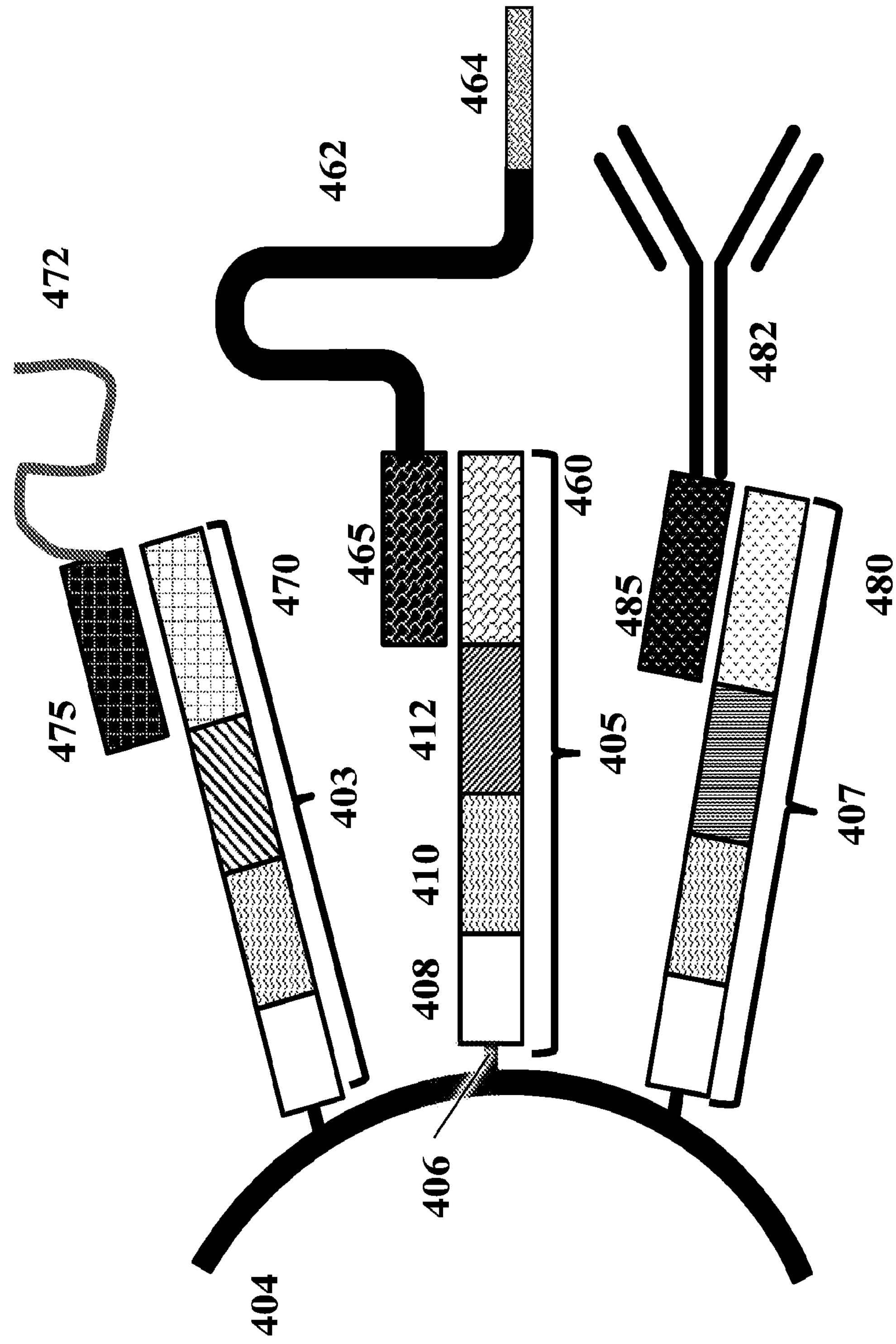
FIG. 4 illustrates another example of a barcode carrying bead.

FIG. 4 illustrates another example of a barcode carrying bead. A nucleic acid barcode molecule 405, such as an oligonucleotide, can be coupled to a bead 404 by a releasable linkage 406, such as, for example, a disulfide linker. The nucleic acid barcode molecule 405 may comprise a first capture sequence 460. The same bead 404 may be coupled (e.g., via releasable linkage) to one or more other nucleic acid molecules 403, 407 comprising other capture sequences. The nucleic acid barcode molecule 405 may be or comprise a barcode. As noted elsewhere herein, the structure of the barcode may comprise a number of sequence elements, such as a functional sequence 408 (e.g., flow cell attachment sequence, sequencing primer sequence, etc.), a barcode sequence 410 (e.g., bead-specific sequence common to bead, partition-specific sequence common to partition, etc.), and a unique molecular identifier 412 (e.g., unique sequence within different molecules attached to the bead), or partial sequences thereof. The capture sequence 460 may be configured to attach to a corresponding capture sequence 465. In some instances, the corresponding capture sequence 465 may be coupled to another molecule that may be an analyte or an intermediary carrier. For example, as illustrated in FIG. 4, the corresponding capture sequence 465 is coupled to a guide RNA molecule 462 comprising a target sequence 464, wherein the target sequence 464 is configured to attach to the analyte. Another oligonucleotide molecule 407 attached to the bead 404 comprises a second capture sequence 480 which is configured to attach to a second corresponding capture sequence 485. As illustrated in FIG. 4, the second corresponding capture sequence 485 is coupled to an antibody 482. In some cases, the antibody 482 may have binding specificity to an analyte (e.g., surface protein). Alternatively, the antibody 482 may not have binding specificity. Another oligonucleotide molecule 403 attached to the bead 404 comprises a third capture sequence 470 which is configured to attach to a third corresponding capture sequence 475. As illustrated in FIG. 4, the third corresponding capture sequence 475 is coupled to a molecule 472. The molecule 472 may or may not be configured to target an analyte. The other oligonucleotide molecules 403, 407 may comprise the other sequences (e.g., functional sequence, barcode sequence, UMI, etc.) described with respect to oligonucleotide molecule 405. While a single oligonucleotide molecule comprising each capture sequence is illustrated in FIG. 4, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 404 may comprise other capture sequences. Alternatively or in addition, the bead 404 may comprise fewer types of capture sequences (e.g., two capture sequences). Alternatively or in addition, the bead 404 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. See, e.g., PCT/US2014/044398, which is hereby incorporated by reference in its entirety.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. See, e.g., PCT/US2014/044398, which is hereby incorporated by reference in its entirety.

As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying nucleic acids (e.g., mRNA, the genomic DNA) from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, beads are provided that each include large numbers of the above described nucleic acid barcode molecules releasably attached to the beads, where all of the nucleic acid barcode molecules attached to a particular bead will include a common nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid barcode molecules into the partitions, as they are capable of carrying large numbers of nucleic acid barcode molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000.000 different barcode sequences, or more. In some cases, the population of beads provides a diverse barcode sequence library that includes about 1,000 to about 10,000 different barcode sequences, about 5,000 to about 50,000 different barcode sequences, about 10,000 to about 100,000 different barcode sequences, about 50,000 to about 1,000,000 different barcode sequences, or about 100,000 to about 10,000,000 different barcode sequences.

Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. In some embodiments, the number of nucleic acid molecules including the barcode sequence on an individual bead is between about 1,000 to about 10,000 nucleic acid molecules, about 5,000 to about 50,000 nucleic acid molecules, about 10,000 to about 100,000 nucleic acid molecules, about 50,000 to about 1,000,000 nucleic acid molecules, about 100,000 to about 10,000,000 nucleic acid molecules, about 1,000,000 to about 1 billion nucleic acid molecules.

Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set. In some embodiments, such different barcode sequences can be associated with a given bead.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid barcode molecules, at least about 5,000 nucleic acid barcode molecules, at least about 10,000 nucleic acid barcode molecules, at least about 50,000 nucleic acid barcode molecules, at least about 100,000 nucleic acid barcode molecules, at least about 500,000 nucleic acids, at least about 1,000,000 nucleic acid barcode molecules, at least about 5,000,000 nucleic acid barcode molecules, at least about 10,000,000 nucleic acid barcode molecules, at least about 50,000,000 nucleic acid barcode molecules, at least about 100,000,000 nucleic acid barcode molecules, at least about 250,000,000 nucleic acid barcode molecules and in some cases at least about 1 billion nucleic acid barcode molecules.

In some cases, the resulting population of partitions provides a diverse barcode sequence library that includes about 1,000 to about 10,000 different barcode sequences, about 5,000 to about 50,000 different barcode sequences, about 10,000 to about 100,000 different barcode sequences, about 50,000 to about 1,000,000 different barcode sequences, or about 100,000 to about 10,000,000 different barcode sequences. Additionally, each partition of the population can include between about 1,000 to about 10,000 nucleic acid barcode molecules, about 5,000 to about 50,000 nucleic acid barcode molecules, about 10,000 to about 100,000 nucleic acid barcode molecules, about 50,000 to about 1,000,000 nucleic acid barcode molecules, about 100,000 to about 10,000,000 nucleic acid barcode molecules, about 1,000,000 to about 1 billion nucleic acid barcode molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

The methods and systems of the present disclosure may comprise microfluidic devices and methods of use thereof, which may be used for co-partitioning biological particles with reagents. Such systems and methods are described in U.S. Patent Publication No. US/20190367997, which is herein incorporated by reference in its entirety for all purposes.

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments of the microfluidic devices described elsewhere herein may be coupled to any of a variety of different fluid sources or receiving components, including reservoirs, tubing, manifolds, or fluidic components of other systems. As will be appreciated, the microfluidic channel structures may have various geometries and/or configurations. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types. e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion-based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., a cell or a nucleus in a polymer matrix), the biological particles may be exposed to an appropriate stimulus to release the biological particles or their contents from a co-partitioned bead. For example, in some cases, a chemical stimulus may be co-partitioned along with an encapsulated biological particle to allow for the degradation of the bead and release of the cell or its contents into the larger partition. In some cases, this stimulus may be the same as the stimulus described elsewhere herein for release of nucleic acid molecules (e.g., oligonucleotides) from their respective bead. In alternative examples, this may be a different and non-overlapping stimulus, in order to allow an encapsulated biological particle to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the biological particle, such as endonucleases to fragment an biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching.

In some cases, template switching can be used to increase the length of a cDNA. In some cases, template switching can be used to append a predefined nucleic acid sequence to the cDNA. Template switching is further described in PCT/US2017/068320, which is hereby incorporated by reference in its entirety. Template switching oligonucleotides may comprise a hybridization region and a template region. Template switching oligonucleotides are further described in PCT/US2017/068320, which is hereby incorporated by reference in its entirety.

Any of the reagents described in this disclosure may be encapsulated in, or otherwise coupled to, a droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, and oligonucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles. In some aspects, this is performed by co-partitioning the individual biological particle or groups of biological particles with the unique identifiers, such as described above (with reference to FIG. 1 or 2).

In some cases, additional beads can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of beads from each source, while ensuring a given pairing or combination of such beads into a partition with a given number of biological particles (e.g., one biological particle and one bead per partition).

In some embodiments, following the generation of barcoded nucleic acid molecules according to methods disclosed herein, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations.

Wells

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). In some embodiments, a well of a fluidic device is fluidically connected to another well of the fluidic device. Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (μL), at most 100 μL, at most 10 μL, at most 1 μL, at most 100 nanoliters (nL), at most 10 nL, at most 1 nL, at most 100 picoliters (pL), at most 10 (pL), or less. The well may be configured to hold a volume of about 1000 μL, about 100 μL, about 10 μL, about 1 μL, about 100 nL, about 10 nL, about 1 nL, about 100 pL, about 10 pL, etc. The well may be configured to hold a volume of at least 10 pL, at least 100 pL, at least 1 nL, at least 10 nL, at least 100 nL, at least 1 μL, at least 10 μL, at least 100 μL, at least 1000 μL, or more. The well may be configured to hold a volume in a range of volumes listed herein, for example, from about 5 nL to about 20 nL, from about 1 nL to about 100 nL, from about 500 pL to about 100 μL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000.000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

Once sealed, the well may be subjected to conditions for further processing of a cell (or cells) in the well. For instance, reagents in the well may allow further processing of the cell, e.g., cell lysis, as further described herein. Alternatively, the well (or wells such as those of a well-based array) comprising the cell (or cells) may be subjected to freeze-thaw cycling to process the cell (or cells), e.g., cell lysis. The well containing the cell may be subjected to freezing temperatures (e.g., 0° C., below 0° C., −5° C., −10° C., −15° C., −20° C., −25° C., −30° C., −35° C., −40° C., −45° C., −50° C., −55° C., −60° C., −65° C., −70° C., −80° C., or −85° C.). Freezing may be performed in a suitable manner, e.g., sub-zero freezer or a dry ice/ethanol bath. Following an initial freezing, the well (or wells) comprising the cell (or cells) may be subjected to freeze-thaw cycles to lyse the cell (or cells). In one embodiment, the initially frozen well (or wells) are thawed to a temperature above freezing (e.g., 4° C. or above, 8° C. or above, 12° C. or above, 16° C. or above, 20° C. or above, room temperature, or 25° C. or above). In another embodiment, the freezing is performed for less than 10 minutes (e.g., 5 minutes or 7 minutes) followed by thawing at room temperature for less than 10 minutes (e.g., 5 minutes or 7 minutes). This freeze-thaw cycle may be repeated a number of times, e.g., 2, 3, 4 or more times, to obtain lysis of the cell (or cells) in the well (or wells). In one embodiment, the freezing, thawing and/or freeze/thaw cycling is performed in the absence of a lysis buffer. Additional disclosure related to freeze-thaw cycling is provided in WO2019165181A1, which is incorporated herein by reference in its entirety.

A well may comprise free reagents and/or reagents encapsulated in, or otherwise coupled to or associated with, beads, or droplets.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a bead, or droplet that comprises a set of reagents that has a similar attribute (e.g., a set of enzymes, a set of minerals, a set of oligonucleotides, a mixture of different barcode molecules, a mixture of identical barcode molecules). In other cases, a bead or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different droplet or bead, or within a solution within a partition (e.g., microwell) of the system.

Figure 5:
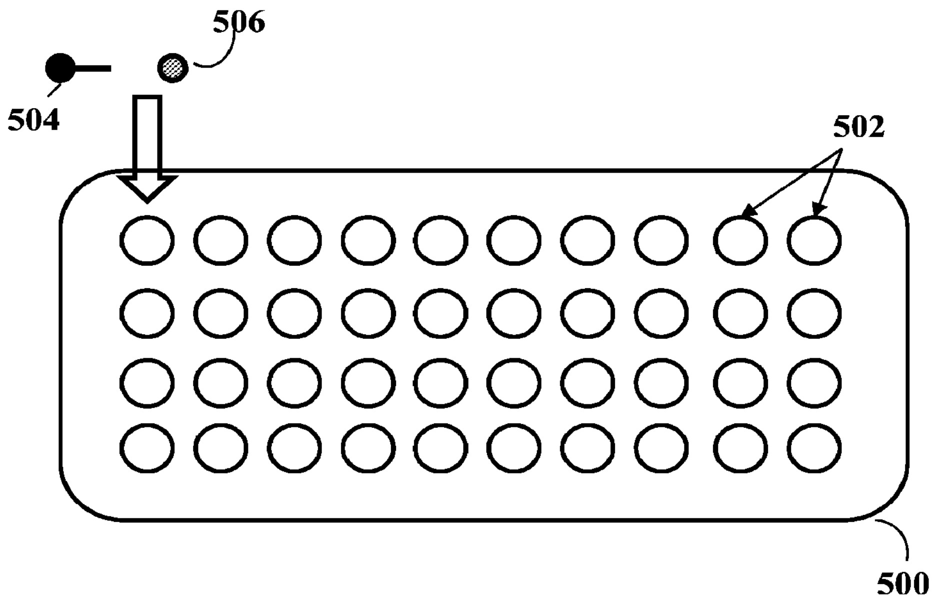
FIG. 5 schematically illustrates an example microwell array.

FIG. 5 schematically illustrates an example of a microwell array. The array can be contained within a substrate 500. The substrate 500 comprises a plurality of wells 502. The wells 502 may be of any size or shape, and the spacing between the wells, the number of wells per substrate, as well as the density of the wells on the substrate 500 can be modified, depending on the particular application. In one such example application, a sample molecule 506, which may comprise a cell or cellular components (e.g., nucleic acid molecules) is co-partitioned with a bead 504, which may comprise a nucleic acid barcode molecule coupled thereto. The wells 502 may be loaded using gravity or other loading technique (e.g., centrifugation, liquid handler, acoustic loading, optoelectronic, etc.). In some instances, at least one of the wells 502 contains a single sample molecule 506 (e.g., cell) and a single bead 504.

Reagents may be loaded into a well either sequentially or concurrently. In some cases, reagents are introduced to the device either before or after a particular operation. In some cases, reagents (which may be provided, in certain instances, in droplets, or beads) are introduced sequentially such that different reactions or operations occur at different steps. The reagents (or droplets, or beads) may also be loaded at operations interspersed with a reaction or operation step. For example, beads (or droplets) comprising reagents for fragmenting polynucleotides (e.g., restriction enzymes) and/or other enzymes (e.g., transposases, ligases, polymerases, etc.) may be loaded into the well or plurality of wells, followed by loading of droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a bead, or droplet. These beads, or droplets may be loaded into a partition (e.g., a microwell) before, after, or concurrently with the loading of a cell, such that each cell is contacted with a different bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or bead may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecules may be attached to a droplet or bead that has been partitioned into the well. The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. In some instances, the nucleic acid barcode molecules may be releasable from the bead or droplet. For instance, the nucleic acid barcode molecules may comprise a chemical cross-linker which may be cleaved upon application of a stimulus (e.g., photo-, magnetic, chemical, biological, stimulus). The nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In some instances nucleic acid barcode molecules attached to a bead or droplet in a well may be hybridized to sample nucleic acid molecules, and the bead with the sample nucleic acid molecules hybridized thereto may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 6:
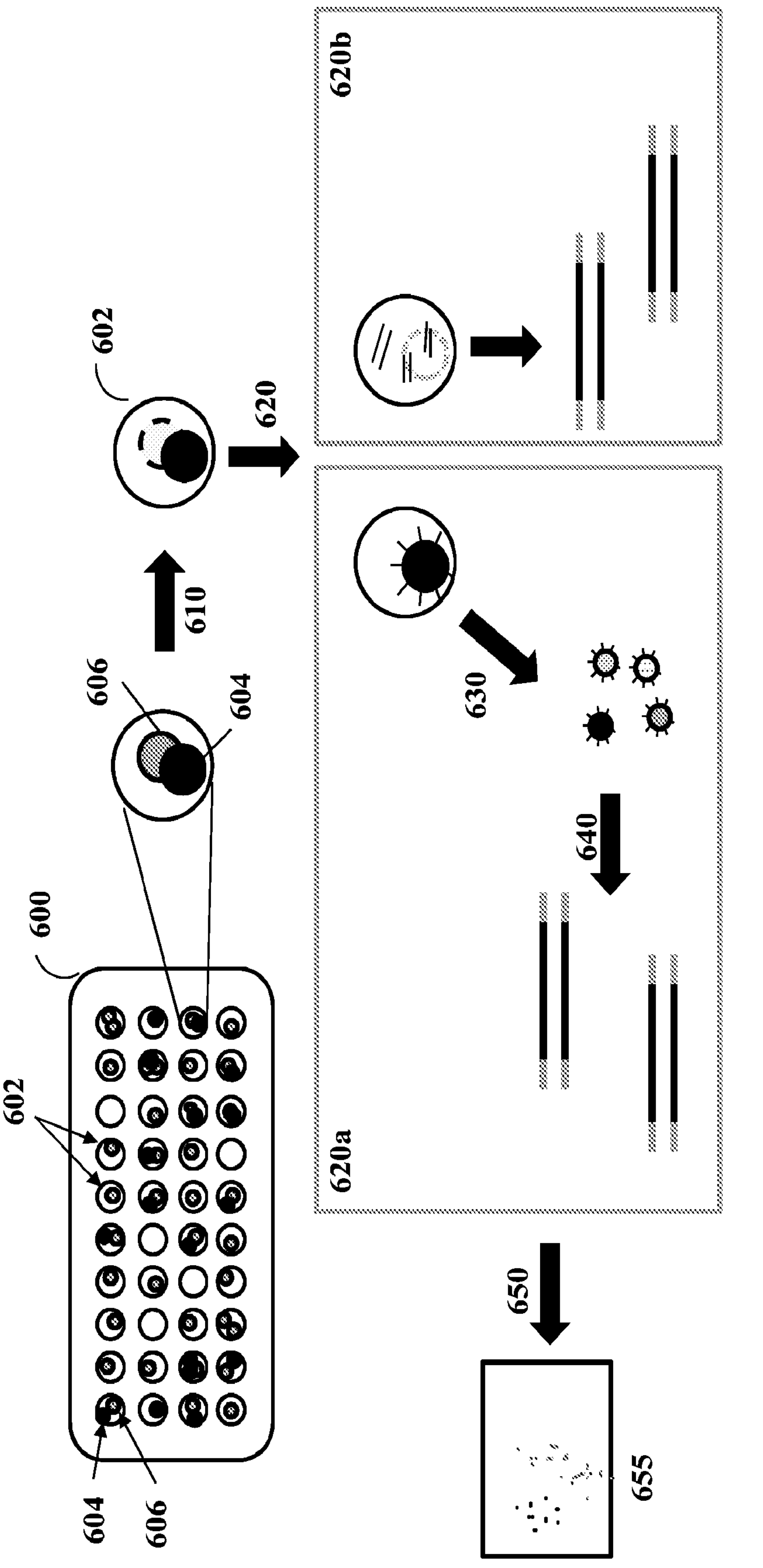
FIG. 6 schematically illustrates an example workflow for processing nucleic acid molecules.

FIG. 6 schematically shows an example workflow for processing nucleic acid molecules within a sample. A substrate 600 comprising a plurality of microwells 602 may be provided. A sample 606 which may comprise a cell, cell bead, cellular components or analytes (e.g., proteins and/or nucleic acid molecules) can be co-partitioned, in a plurality of microwells 602, with a plurality of beads 604 comprising nucleic acid barcode molecules. During process 610, the sample 606 may be processed within the partition. For instance, in the case of live cells, the cell may be subjected to conditions sufficient to lyse the cells and release the analytes contained therein. In process 620, the bead 604 may be further processed. By way of example, processes 620*a* and 620*b* schematically illustrate different workflows, depending on the properties of the bead 604.

In 620*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 630, the beads 604 from multiple wells 602 may be collected and pooled. Further processing may be performed in process 640. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

In 620*b*, the bead comprises nucleic acid barcode molecules that are releasably attached thereto, as described below. The bead may degrade or otherwise release the nucleic acid barcode molecules into the well 602; the nucleic acid barcode molecules may then be used to barcode nucleic acid molecules within the well 602. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

Sample and Cell Processing

A sample may derive from any useful source including any subject, such as a human subject. A sample may comprise material (e.g., one or more biological particles) from one or more different sources, such as one or more different subjects. Multiple samples, such as multiple samples from a single subject (e.g., multiple samples obtained in the same or different manners from the same or different bodily locations, and/or obtained at the same or different times (e.g., seconds, minutes, hours, days, weeks, months, or years apparat)), or multiple samples from different subjects, may be obtained for analysis as described herein. For example, a first sample may be obtained from a subject at a first time and a second sample may be obtained from the subject at a second time later than the first time. The first time may be before a subject undergoes a treatment regimen or procedure (e.g., to address a disease or condition), and the second time may be during or after the subject undergoes the treatment regimen or procedure. In another example, a first sample may be obtained from a first bodily location or system of a subject (e.g., using a first collection technique) and a second sample may be obtained from a second bodily location or system of the subject (e.g., using a second collection technique), which second bodily location or system may be different than the first bodily location or system. In another example, multiple samples may be obtained from a subject at a same time from the same or different bodily locations. Different samples, such as different subjects collected from different bodily locations of a same subject, at different times, from multiple different subjects, and/or using different collection techniques, may undergo the same or different processing (e.g., as described herein). For example, a first sample may undergo a first processing protocol and a second sample may undergo a second processing protocol. In another example, a portion of a sample may undergo a first processing protocol and a second portion of the sample may undergo a second processing protocol.

A sample may be a biological sample, such as a cell sample (e.g., as described herein). A sample may include one or more biological particles, such as one or more cells and/or cellular constituents, such as one or more cell nuclei. A sample may be a tissue sample. For example, a sample may comprise a plurality of biological particles, such as a plurality of cells and/or cellular constituents. Biological particles (e.g., cells or cellular constituents, such as cell nuclei) of a sample may be of a single type or a plurality of different types. For example, cells of a sample may include one or more different types or blood cells.

Cells and cellular constituents of a sample may be of any type. For example, a cell or cellular constituent may be a vertebral, mammalian, fungal, plant, bacterial, or other cell type. In some cases, the cell is a mammalian cell, such as a human cell. The cell may be, for example, a stem cell, liver cell, nerve cell, bone cell, blood cell, reproductive cell, skin cell, skeletal muscle cell, cardiac muscle cell, smooth muscle cell, hair cell, hormone-secreting cell, or glandular cell. The cell may be, for example, an erythrocyte (e.g., red blood cell), a megakaryocyte (e.g., platelet precursor), a monocyte (e.g., white blood cell), a leukocyte, a B cell, a T cell (such as a helper, suppressor, cytotoxic, or natural killer T cell), an osteoclast, a dendritic cell, a connective tissue macrophage, an epidermal Langerhans cell, a microglial cell, a granulocyte, a hybridoma cell, a mast cell, a natural killer cell, a reticulocyte, a hematopoietic stem cell, a myoepithelial cell, a myeloid-derived suppressor cell, a platelet, a thymocyte, a satellite cell, an epithelial cell, an endothelial cell, an epididymal cell, a kidney cell, a liver cell, an adipocyte, a lipocyte, or a neuron cell. In some cases, the cell may be associated with a cancer, tumor, or neoplasm. In some cases, the cell may be associated with a fetus. In some cases, the cell may be a Jurkat cell.

A biological sample may include a plurality of cells having different dimensions and features. In some cases, processing of the biological sample, such as cell separation and sorting (e.g., as described herein), may affect the distribution of dimensions and cellular features included in the sample by depleting cells having certain features and dimensions and/or isolating cells having certain features and dimensions.

A sample may undergo one or more processes in preparation for analysis (e.g., as described herein), including, but not limited to, filtration, selective precipitation, purification, centrifugation, permeabilization, isolation, agitation, heating, and/or other processes. For example, a sample may be filtered to remove a contaminant or other materials. In an example, a filtration process may comprise the use of microfluidics (e.g., to separate biological particles of different sizes, types, charges, or other features).

In an example, a sample comprising one or more cells may be processed to separate the one or more cells from other materials in the sample (e.g., using centrifugation and/or another process). In some cases, cells and/or cellular constituents of a sample may be processed to separate and/or sort groups of cells and/or cellular constituents, such as to separate and/or sort cells and/or cellular constituents of different types. Examples of cell separation include, but are not limited to, separation of white blood cells or immune cells from other blood cells and components, separation of circulating tumor cells from blood, and separation of bacteria from bodily cells and/or environmental materials. A separation process may comprise a positive selection process (e.g., targeting of a cell type of interest for retention for subsequent downstream analysis, such as by use of a monoclonal antibody that targets a surface marker of the cell type of interest), a negative selection process (e.g., removal of one or more cell types and retention of one or more other cell types of interest), and/or a depletion process (e.g., removal of a single cell type from a sample, such as removal of red blood cells from peripheral blood mononuclear cells).

Separation of one or more different types of cells may comprise, for example, centrifugation, filtration, microfluidic-based sorting, flow cytometry, fluorescence-activated cell sorting (FACS), magnetic-activated cell sorting (MACS), buoyancy-activated cell sorting (BACS), or any other useful method.

For example, a flow cytometry method may be used to detect cells and/or cellular constituents based on a parameter such as a size, morphology, or protein expression. Flow cytometry-based cell sorting may comprise injecting a sample into a sheath fluid that conveys the cells and/or cellular constituents of the sample into a measurement region one at a time. In the measurement region, a light source such as a laser may interrogate the cells and/or cellular constituents and scattered light and/or fluorescence may be detected and converted into digital signals. A nozzle system (e.g., a vibrating nozzle system) may be used to generate droplets (e.g., aqueous droplets) comprising individual cells and/or cellular constituents. Droplets including cells and/or cellular constituents of interest (e.g., as determined via optical detection) may be labeled with an electric charge (e.g., using an electrical charging ring), which charge may be used to separate such droplets from droplets including other cells and/or cellular constituents. For example, FACS may comprise labeling cells and/or cellular constituents with fluorescent markers (e.g., using internal and/or external biomarkers). Cells and/or cellular constituents may then be measured and identified one by one and sorted based on the emitted fluorescence of the marker or absence thereof. MACS may use micro- or nano-scale magnetic particles to bind to cells and/or cellular constituents (e.g., via an antibody interaction with cell surface markers) to facilitate magnetic isolation of cells and/or cellular constituents of interest from other components of a sample (e.g., using a column-based analysis). BACS may use microbubbles (e.g., glass microbubbles) labeled with antibodies to target cells of interest. Cells and/or cellular components coupled to microbubbles may float to a surface of a solution, thereby separating target cells and/or cellular components from other components of a sample. Cell separation techniques may be used to enrich for populations of cells of interest (e.g., prior to partitioning, as described herein). For example, a sample comprising a plurality of cells including a plurality of cells of a given type may be subjected to a positive separation process. The plurality of cells of the given type may be labeled with a fluorescent marker (e.g., based on an expressed cell surface marker or another marker) and subjected to a FACS process to separate these cells from other cells of the plurality of cells. The selected cells may then be subjected to subsequent partition-based analysis (e.g., as described herein) or other downstream analysis. The fluorescent marker may be removed prior to such analysis or may be retained. The fluorescent marker may comprise an identifying feature, such as a nucleic acid barcode sequence and/or unique molecular identifier.

In another example, a first sample comprising a first plurality of cells including a first plurality of cells of a given type (e.g., immune cells expressing a particular marker or combination of markers) and a second sample comprising a second plurality of cells including a second plurality of cells of the given type may be subjected to a positive separation process. The first and second samples may be collected from the same or different subjects, at the same or different types, from the same or different bodily locations or systems, using the same or different collection techniques. For example, the first sample may be from a first subject and the second sample may be from a second subject different than the first subject. The first plurality of cells of the first sample may be provided a first plurality of fluorescent markers configured to label the first plurality of cells of the given type. The second plurality of cells of the second sample may be provided a second plurality of fluorescent markers configured to label the second plurality of cells of the given type. The first plurality of fluorescent markers may include a first identifying feature, such as a first barcode, while the second plurality of fluorescent markers may include a second identifying feature, such as a second barcode, that is different than the first identifying feature. The first plurality of fluorescent markers and the second plurality of fluorescent markers may fluoresce at the same intensities and over the same range of wavelengths upon excitation with a same excitation source (e.g., light source, such as a laser). The first and second samples may then be combined and subjected to a FACS process to separate cells of the given type from other cells based on the first plurality of fluorescent markers labeling the first plurality of cells of the given type and the second plurality of fluorescent markers labeling the second plurality of cells of the given type. Alternatively, the first and second samples may undergo separate FACS processes and the positively selected cells of the given type from the first sample and the positively selected cells of the given type from the second sample may then be combined for subsequent analysis. The encoded identifying features of the different fluorescent markers may be used to identify cells originating from the first sample and cells originating from the second sample. For example, the first and second identifying features may be configured to interact (e.g., in partitions, as described herein) with nucleic acid barcode molecules (e.g., as described herein) to generate barcoded nucleic acid products detectable using. e.g., nucleic acid sequencing.

Multiplexing

The present disclosures provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize biological particles and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, an MHC molecule complex, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In some aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more biological particles may be used to characterize a biological particle as belonging to a particular set of biological particles. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling an biological particle may comprise subjecting the antibody-linked barcode molecule or the epitope binding fragment-linked barcode molecule to conditions suitable for binding the antibody to a molecule present on a surface of the biological particle. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 μM, 90 μM, 80 μM, 70 μM, 60 μM, 50 μM, 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 μM.

In another example, a reporter oligonucleotide may be coupled to a cell-penetrating peptide (CPP), and labeling cells may comprise delivering the CPP coupled reporter oligonucleotide into a biological particle. Labeling biological particles may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells may comprise subjecting the fluorophore-linked barcode molecule to conditions suitable for binding the fluorophore to the surface of the biological particle. In some instances, fluorophores can interact strongly with lipid bilayers and labeling biological particles may comprise subjecting the fluorophore-linked barcode molecule to conditions such that the fluorophore binds to or is inserted into a membrane of the biological particle. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLOS One. 2014 Feb. 4; 9(2): e87649, which is hereby incorporated by reference in its entirety for all purposes, for a description of organic fluorophores.

A reporter oligonucleotide may be coupled to a lipophilic molecule, and labeling biological particles may comprise delivering the nucleic acid barcode molecule to a membrane of the biological particle or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and biological particle may be such that the biological particle retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular biological particle, population, or sample. The biological particles may be incubated with a plurality of libraries and a given biological particle may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment), e.g., via a linker, using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31 (2): 708-715, which is entirely incorporated herein by reference for all purposes. Likewise, protein and peptide biotinylation techniques have been developed and are readily available. Sec, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 11:
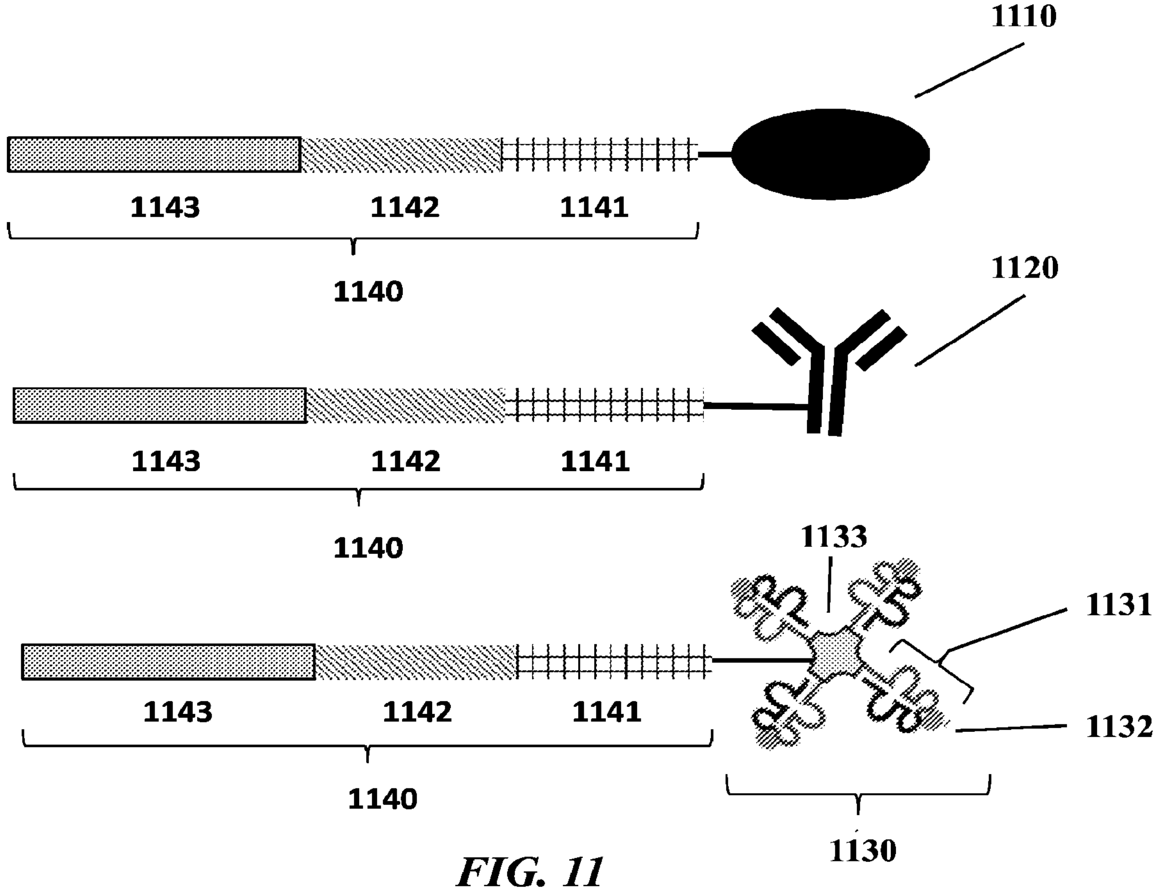
FIG. 11 schematically illustrates example labelling agents with nucleic acid molecules attached thereto.

FIG. 11 describes exemplary labelling agents (1110, 1120, 1130) comprising reporter oligonucleotides (1140) attached thereto. Labelling agent 1110 (e.g., any of the labelling agents described herein) is attached (either directly, e.g., covalently attached, or indirectly) to reporter oligonucleotide 1140. Reporter oligonucleotide 1140 may comprise barcode sequence 1142 that identifies labelling agent 1110. Reporter oligonucleotide 1140 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 11, in some instances, reporter oligonucleotide 1140 conjugated to a labelling agent (e.g., 1110, 1120, 1130) comprises a functional sequence 1141 (e.g., a primer sequence), a barcode sequence that identifies the labelling agent (e.g., 1110, 1120, 1130), and functional sequence 1143. Functional sequence 1143 can be a reporter capture handle sequence configured to hybridize to a complementary sequence, such as a complementary sequence present on a nucleic acid barcode molecule 1190 (not shown), such as those described elsewhere herein. In some instances, nucleic acid barcode molecule 1190 is attached to a support (e.g., a bead, such as a gel bead), such as those described elsewhere herein. For example, nucleic acid barcode molecule 1190 may be attached to the support via a releasable linkage (e.g., comprising a labile bond), such as those described elsewhere herein. In some instances, reporter oligonucleotide 1140 comprises one or more additional functional sequences, such as those described above.

In some instances, the labelling agent 1110 is a protein or polypeptide (e.g., an MHC molecule complex, an antigen or prospective antigen) comprising reporter oligonucleotide 1140. Reporter oligonucleotide 1140 comprises barcode sequence 1142 that identifies polypeptide 1110 and can be used to infer the presence of an analyte, e.g., a binding partner of polypeptide 1110 (i.e., a molecule or compound to which polypeptide 1110 can bind). In some instances, the labelling agent 1110 is a lipophilic moiety (e.g., cholesterol) comprising reporter oligonucleotide 1140, where the lipophilic moiety is selected such that labelling agent 1110 integrates into a membrane of a cell or nucleus. Reporter oligonucleotide 1140 comprises barcode sequence 1142 that identifies lipophilic moiety 1110 which in some instances is used to tag cells (e.g., groups of cells, cell samples, etc.) and may be used for multiplex analyses as described elsewhere herein. In some instances, the labelling agent is an antibody 1120 (or an epitope binding fragment thereof) comprising reporter oligonucleotide 1140. Reporter oligonucleotide 1140 comprises barcode sequence 1142 that identifies antibody 1120 and can be used to infer the presence of, e.g., a target of antibody 1120 (i.e., a molecule or compound to which antibody 1120 binds). In other embodiments, labelling agent 1130 comprises an MHC molecule 1131 comprising peptide 1132 and reporter oligonucleotide 1140 that identifies peptide 1132. In some instances, the MHC molecule is coupled to a support 1133. In some instances, support 1133 may be or comprise a polypeptide, such as avidin, neutravidin, streptavidin, or a polysaccharide, such as dextran. In some embodiments, support 1133 further comprises a detectable label, e.g., a detectable label described herein, e.g., a fluorescent label. In some instances, reporter oligonucleotide 1140 may be directly or indirectly coupled to MHC labelling agent 1130 in any suitable manner. For example, reporter oligonucleotide 1140 may be coupled to MHC molecule 1131, support 1133, or peptide 1132. In some embodiments, labelling agent 1130 comprises a plurality of MHC molecules as described herein, (e.g. is an MHC multimer, which may be coupled to a support (e.g., 1133)). In some embodiments, reporter oligonucleotide 1140 and MHC molecule 1130 are attached to the polypeptide or polysaccharide of support 1133. In some embodiments, reporter oligonucleotide 1140 and MHC molecule 1130 are attached to the detectable label of support 1133. In some embodiments, reporter oligonucleotide 1140 and MHC molecule 1130 are attached to the polypeptide or polysaccharide of support 1133. In some embodiments, reporter oligonucleotide 1140 and MHC molecule 1130 are attached to the detectable label of support 1133. There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 12A:
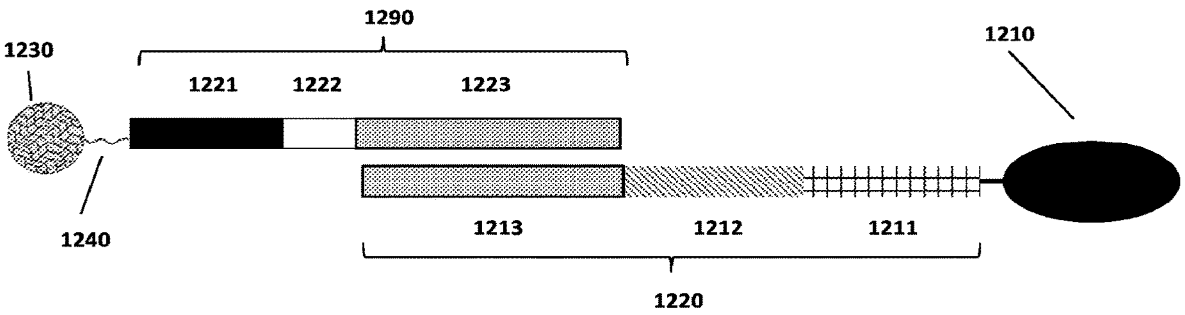
FIG. 12A schematically shows an example of labelling agents.
Figure 12B:
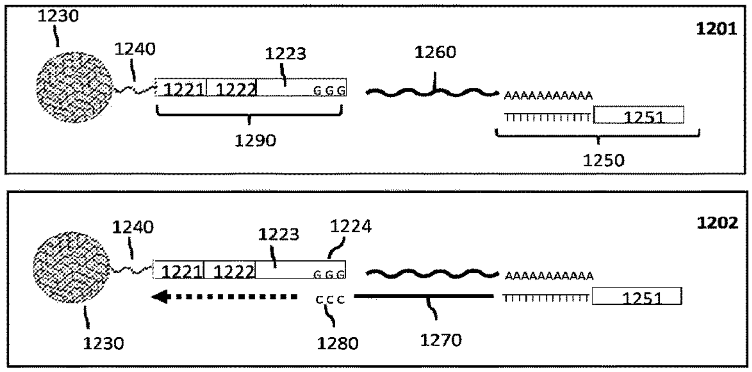
FIG. 12B schematically shows another example workflow for processing nucleic acid molecules.
Figure 12C:
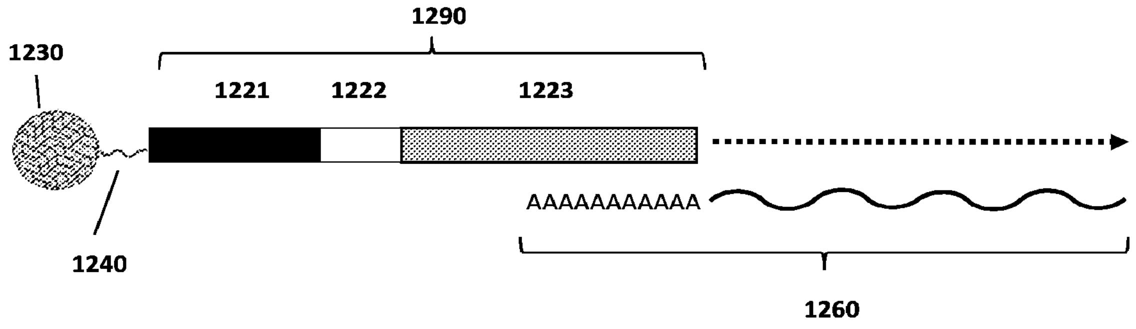
FIG. 12C schematically shows another example workflow for processing nucleic acid molecules.
Figure 13:
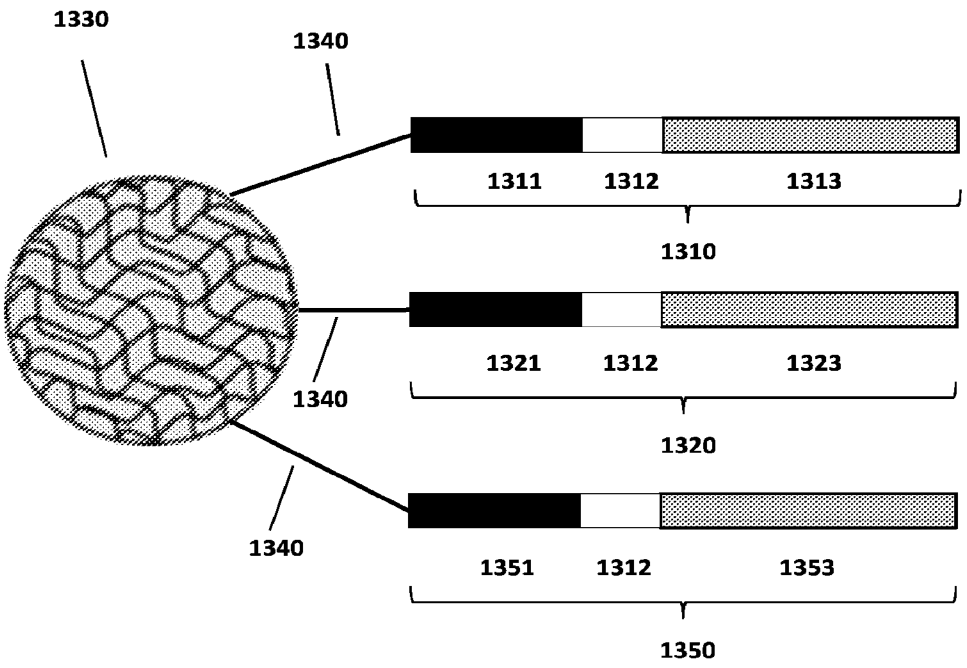
FIG. 13 schematically shows another example of a barcode-carrying bead.

FIG. 13 illustrates another example of a barcode carrying bead. In some embodiments, analysis of multiple analytes (e.g., RNA and one or more analytes using labelling agents described herein) may comprise nucleic acid barcode molecules as generally depicted in FIG. 13. In some embodiments, nucleic acid barcode molecules 1310 and 1320 are attached to support 1330 via a releasable linkage 1340 (e.g., comprising a labile bond) as described elsewhere herein. Nucleic acid barcode molecule 1310 may comprise adapter sequence 1311, barcode sequence 1312 and capture sequence 1313. Nucleic acid barcode molecule 1320 may comprise adapter sequence 1321, barcode sequence 1312, and capture sequence 1323, wherein capture sequence 1323 comprises a different sequence than capture sequence 1313. In some instances, adapter 1311 and adapter 1321 comprise the same sequence. In some instances, adapter 1311 and adapter 1321 comprise different sequences. Although support 1330 is shown comprising nucleic acid barcode molecules 1310 and 1320, any suitable number of barcode molecules comprising common barcode sequence 1312 are contemplated herein. For example, in some embodiments, support 1330 further comprises nucleic acid barcode molecule 1350. Nucleic acid barcode molecule 1350 may comprise adapter sequence 1351, barcode sequence 1312 and capture sequence 1353, wherein capture sequence 1353 comprises a different sequence than capture sequence 1313 and 1323. In some instances, nucleic acid barcode molecules (e.g., 1310, 1320, 1350) comprise one or more additional functional sequences, such as a UMI or other sequences described herein. The nucleic acid barcode molecules 1310, 1320 or 1350 may interact with analytes as described elsewhere herein, for example, as depicted in FIGS. 12A-C.

Referring to FIG. 12A, in an instance where cells are labelled with labeling agents, capture sequence 1223 may be complementary to an adapter sequence of a reporter oligonucleotide. Cells may be contacted with one or more reporter oligonucleotide 1220 conjugated labelling agents 1210 (e.g., MHC molecule complex, polypeptide, antibody, or others described elsewhere herein). In some cases, the cells may be further processed prior to barcoding. For example, such processing steps may include one or more washing and/or cell sorting steps. In some instances, a cell that is bound to labelling agent 1210 which is conjugated to oligonucleotide 1220 and support 1230 (e.g., a bead, such as a gel bead) comprising nucleic acid barcode molecule 1290 is partitioned into a partition amongst a plurality of partitions (e.g., a droplet of a droplet emulsion or a well of a microwell array). In some instances, the partition comprises at most a single cell bound to labelling agent 1210. In some instances, reporter oligonucleotide 1220 conjugated to labelling agent 1210 (e.g., polypeptide, an antibody, pMHC molecule such as an MHC multimer, etc.) comprises a first adapter sequence 1211 (e.g., a primer sequence), a barcode sequence 1212 that identifies the labelling agent 1210 (e.g., the polypeptide, antibody, or peptide of a pMHC molecule or complex), and an capture handle sequence 1213. Capture handle sequence 1213 may be configured to hybridize to a complementary sequence, such as a capture sequence 1223 present on a nucleic acid barcode molecule 1290. In some instances, oligonucleotide 1220 comprises one or more additional functional sequences, such as those described elsewhere herein.

Barcoded nucleic acid molecules may be generated (e.g., via a nucleic acid reaction, such as nucleic acid extension or ligation) from the constructs described in FIGS. 12A-C. For example, capture handle sequence 1213 may then be hybridized to complementary sequence, such as capture sequence 1223 to generate (e.g., via a nucleic acid reaction, such as nucleic acid extension or ligation) a barcoded nucleic acid molecule comprising cell (e.g., partition specific) barcode sequence 1222 (or a reverse complement thereof) and reporter barcode sequence 1212 (or a reverse complement thereof). In some embodiments, the nucleic acid barcode molecule 1290 (e.g., partition-specific barcode molecule) further includes a UMI (not shown). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 12A-C, or a combination of workflows for an individual analyte, as described elsewhere herein. For example, by using a combination of the workflows as generally depicted in FIGS. 12A-C, multiple analytes can be analyzed.

In some instances, analysis of an analyte (e.g. a nucleic acid, a polypeptide, a carbohydrate, a lipid, TCR, BCR, Ab or antigen binding fragment thereof, etc.) comprises a workflow as generally depicted in FIG. 12A. A nucleic acid barcode molecule 1290 may be co-partitioned with the one or more analytes. In some instances, nucleic acid barcode molecule 1290 is attached to a support 1230 (e.g., a bead, such as a gel bead), such as those described elsewhere herein. For example, nucleic acid barcode molecule 1290 may be attached to support 1230 via a releasable linkage 1240 (e.g., comprising a labile bond), such as those described elsewhere herein. Nucleic acid barcode molecule 1290 may comprise a functional sequence 1221 and optionally comprise other additional sequences, for example, a barcode sequence 1222 (e.g., common barcode, partition-specific barcode, or other functional sequences described elsewhere herein), and/or a UMI sequence (not shown). The nucleic acid barcode molecule 1290 may comprise a capture sequence 1223 that may be complementary to another nucleic acid sequence, such that it may hybridize to a particular sequence, e.g., capture handle sequence 1213.

For example, capture sequence 1223 may comprise a poly-T sequence and may be used to hybridize to mRNA. Referring to FIG. 12C, in some embodiments, nucleic acid barcode molecule 1290 comprises capture sequence 1223 complementary to a sequence of RNA molecule 1260 from a cell. In some instances, capture sequence 1223 comprises a sequence specific for an RNA molecule. Capture sequence 1223 may comprise a known or targeted sequence or a random sequence. In some instances, a nucleic acid extension reaction may be performed, thereby generating a barcoded nucleic acid product comprising capture sequence 1223, the functional sequence 1221, barcode sequence 1222, any other functional sequence, and a sequence corresponding to the RNA molecule 1260.

In another example, capture sequence 1223 may be complementary to an overhang sequence or an adapter sequence that has been appended to an analyte. For example, referring to FIG. 12B, panel 1201, in some embodiments, primer 1250 comprises a sequence complementary to a sequence of nucleic acid molecule 1260 (such as an RNA encoding for a TCR or BCR sequence) from a biological particle. In some instances, primer 1250 comprises one or more sequences 1251 that are not complementary to RNA molecule 1260. Sequence 1251 may be a functional sequence as described elsewhere herein, for example, an adapter sequence, a sequencing primer sequence, or a sequence the facilitates coupling to a flow cell of a sequencer. In some instances, primer 1250 comprises a poly-T sequence. In some instances, primer 1250 comprises a sequence complementary to a target sequence in an RNA molecule. In some instances, primer 1250 comprises a sequence complementary to a region of an immune molecule, such as the constant region of a TCR or BCR sequence. Primer 1250 is hybridized to nucleic acid molecule 1260 and complementary molecule 1270 is generated (see Panel 1202). For example, complementary molecule 1270 may be cDNA generated in a reverse transcription reaction. In some instances, an additional sequence may be appended to complementary molecule 1270. For example, the reverse transcriptase enzyme may be selected such that several non-templated bases 1280 (e.g., a poly-C sequence) are appended to the cDNA. In another example, a terminal transferase may also be used to append the additional sequence. Nucleic acid barcode molecule 1290 comprises a sequence 1224 complementary to the non-templated bases, and the reverse transcriptase performs a template switching reaction onto nucleic acid barcode molecule 1290 to generate a barcoded nucleic acid molecule comprising cell (e.g., partition specific) barcode sequence 1222 (or a reverse complement thereof) and a sequence of complementary molecule 1270 (or a portion thereof). In some instances, sequence 1223 comprises a sequence complementary to a region of an immune molecule, such as the constant region of a TCR or BCR sequence. Sequence 1223 is hybridized to nucleic acid molecule 1260 and a complementary molecule 1270 is generated. For example complementary molecule 1270 may be generated in a reverse transcription reaction generating a barcoded nucleic acid molecule comprising cell (e.g., partition specific) barcode sequence 1222 (or a reverse complement thereof) and a sequence of complementary molecule 1270 (or a portion thereof). Additional methods and compositions suitable for barcoding cDNA generated from mRNA transcripts including those encoding V (D) J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No. 2019/0367969, each of which applications is herein entirely incorporated by reference for all purposes.

In some embodiments, biological particles (e.g., cells, nuclei) from a plurality of samples (e.g., a plurality of subjects) can be pooled, sequenced, and demultiplexed by identifying mutational profiles associated with individual samples and mapping sequence data from single biological particles to their source based on their mutational profile. Sec, e.g., Xu J. et al., Genome Biology Vol. 20, 290 (2019); Huang Y. et al., Genome Biology Vol. 20, 273 (2019); and Heaton et al., Nature Methods volume 17, pages 615-620 (2020).

Gene expression data can reflect the underlying genome and mutations and structural variants therein. As a result, the variation inherent in the captured and sequenced RNA molecules can be used to identify genotypes de novo or used to assign molecules to genotypes that were known a priori. In some embodiments, allelic variation that is present due to haplotypic states (including linkage disequilibrium of the human leucocyte antigen loci (HLA), immune receptor loci (BCR), and other highly polymorphic regions of the genome), can also be used for demultiplexing. Expressed B cell receptors can be used to infer germline alleles from unrelated individuals, which information may be used for demultiplexing.

Combinatorial Barcoding

In some instances, barcoding of a nucleic acid molecule may be done using a combinatorial approach. In such instances, one or more nucleic acid molecules (which may be comprised in a biological particle, e.g, cell, e.g., a fixed cell, organelle, nucleus or cell bead) may be partitioned (e.g., in a first set of partitions. e.g., wells or droplets) with one or more first nucleic acid barcode molecules (optionally coupled to a bead). The first nucleic acid barcode molecules or derivative thereof (e.g., complement, reverse complement) may then be attached to the one or more nucleic acid molecules, thereby generating barcoded nucleic acid molecules, e.g., using the processes described herein. The first nucleic acid barcode molecules may be partitioned to the first set of partitions such that a nucleic acid barcode molecule, of the first nucleic acid barcode molecules, that is in a partition comprises a barcode sequence that is unique to the partition among the first set of partitions. Each partition may comprise a unique barcode sequence. For example, a set of first nucleic acid barcode molecules partitioned to a first partition in the first set of partitions may each comprise a common barcode sequence that is unique to the first partition among the first set of partitions, and a second set of first nucleic acid barcode molecules partitioned to a second partition in the first set of partitions may each comprise another common barcode sequence that is unique to the second partition among the first set of partitions. Such barcode sequence (unique to the partition) may be useful in determining the cell or partition from which the one or more nucleic acid molecules (or derivatives thereof) originated.

The barcoded nucleic acid molecules from multiple partitions of the first set of partitions may be pooled and re-partitioned (e.g., in a second set of partitions, e.g., one or more wells or droplets) with one or more second nucleic acid barcode molecules. The second nucleic acid barcode molecules or derivative thereof may then be attached to the barcoded nucleic acid molecules. As with the first nucleic acid barcode molecules during the first round of partitioning, the second nucleic acid barcode molecules may be partitioned to the second set of partitions such that a nucleic acid barcode molecule, of the second nucleic acid barcode molecules, that is in a partition comprises a barcode sequence that is unique to the partition among the second set of partitions. Such barcode sequence may also be useful in determining the cell or partition from which the one or more nucleic acid molecules or first barcoded nucleic acid molecules originated. The barcoded nucleic acid molecules may thus comprise two barcode sequences (e.g., from the first nucleic acid barcode molecules and the second nucleic acid barcode molecules).

Additional barcode sequences may be attached to the barcoded nucleic acid molecules by repeating the processes any number of times (e.g., in a split-and-pool approach), thereby combinatorically synthesizing unique barcode sequences to barcode the one or more nucleic acid molecules. For example, combinatorial barcoding may comprise at least 1, 2, 3, 4, 5, 6, 7, 8, 9, 10 or more operations of splitting (e.g., partitioning) and/or pooling (e.g., from the partitions). Additional examples of combinatorial barcoding may also be found in International Patent Publication Nos. WO2019/165318, each of which is herein entirely incorporated by reference for all purposes. Another example of combinatorial barcoding is described in Rosenberg et al., Science 360, 176-182 (2018).

Beneficially, the combinatorial barcode approach may be useful for generating greater barcode diversity, and synthesizing unique barcode sequences on nucleic acid molecules derived from a cell or partition. For example, combinatorial barcoding comprising three operations, each with 100 partitions, may yield up to $10^6$ unique barcode combinations. In some instances, the combinatorial barcode approach may be helpful in determining whether a partition contained only one cell or more than one cell. For instance, the sequences of the first nucleic acid barcode molecule and the second nucleic acid barcode molecule may be used to determine whether a partition comprised more than one cell. For instance, if two nucleic acid molecules comprise different first barcode sequences but the same second barcode sequences, it may be inferred that the second set of partitions comprised two or more cells.

In some instances, combinatorial barcoding may be achieved in the same compartment. For instance, a unique nucleic acid molecule comprising one or more nucleic acid bases may be attached to a nucleic acid molecule (e.g., a sample or target nucleic acid molecule) in successive operations within a partition (e.g., droplet or well) to generate a barcoded nucleic acid molecule. A second unique nucleic acid molecule comprising one or more nucleic acid bases may be attached to the barcoded nucleic acid molecule. In some instances, all the reagents for barcoding and generating combinatorially barcoded molecules may be provided in a single reaction mixture, or the reagents may be provided sequentially.

In some instances, cell beads comprising nucleic acid molecules may be barcoded. Methods and systems for barcoding cell beads are further described in PCT/US2018/067356 and U.S. Pat. Pub. No. 2019/0330694, which are hereby incorporated by reference in its entirety.

In some instances wherein a partition is a volume wherein diffusion of contents beyond the volume is inhibited, the partition contains a diffusion resistant material. Such partition may also be referred to herein as a diffusion resistant partition. The diffusion resistant material may have an increased viscosity. The diffusion resistant material may be or comprise a matrix, e.g., a polymeric matrix, or a gel. Suitable polymers or gels are disclosed herein. In some embodiments, a diffusion resistant partition comprises a single biological particle and a single bead, the single bead comprising a plurality of nucleic acid barcode molecules comprising a partition specific barcode sequence. In some embodiments the partition specific barcode sequence is unique to the diffusion resistant partition. In some embodiments, partitioning comprises contacting a plurality of biological particles with a plurality of beads in a diffusion resistant material to provide a diffusion resistant partition comprising a single biological particle and a single bead. In some embodiments, partitioning comprises contacting a plurality of biological particles with a plurality of beads in a liquid comprising a polymeric precursor material that may be capable of being formed into a gel or other solid or semi-solid matrix, and subjecting the liquid to conditions sufficient to polymerize or gel the precursors, e.g., as described herein. In some embodiments, the biological particle may be lysed or permeabilized in the diffusion resistant partition. In some embodiments, a nucleic acid analyte of the biological particle (which may include a reporter oligonucleotide associated with a labelling agent disclosed herein) may be coupled with a nucleic acid barcode molecule in the diffusion resistant partition. In some cases, further processing, e.g., generation of barcoded nucleic acid molecules, may be performed in the diffusion resistant partition or in bulk. For example, nucleic acid analytes, once coupled to nucleic acid barcode molecules in diffusion resistant partitions, may be pooled and then subjected to further processing in bulk (e.g. extension, reverse transcription, or other processing) to generate barcoded nucleic acid molecules. For other example, nucleic acid analytes, one coupled to nucleic acid barcode molecules in diffusion resistant partitions, may be subjected to further processing in the diffusion resistant partitions to generate barcoded nucleic acid molecules.

A sample may be a fixed sample. For example, a sample may comprise a plurality of fixed samples, such as a plurality of fixed cells or fixed nuclei. Alternatively or in addition, a sample may comprise a fixed tissue. Fixation of cell or cellular constituent, or a tissue comprising a plurality of cells or nuclei, may comprise application of a chemical species or chemical stimulus. The term "fixed" as used herein with regard to biological samples generally refers to the state of being preserved from decay and/or degradation. "Fixation" generally refers to a process that results in a fixed sample, and in some instances can include contacting the biomolecules within a biological sample with a fixative (or fixation reagent) for some amount of time, whereby the fixative results in covalent bonding interactions such as crosslinks between biomolecules in the sample. A "fixed biological sample" may generally refer to a biological sample that has been contacted with a fixation reagent or fixative. For example, a formaldehyde-fixed biological sample has been contacted with the fixation reagent formaldehyde. "Fixed cells" or "fixed tissues" generally refer to cells or tissues that have been in contact with a fixative under conditions sufficient to allow or result in the formation of intra- and inter-molecular covalent crosslinks between biomolecules in the biological sample. Generally, contact of biological sample (e.g., a cell or nucleus) with a fixation reagent (e.g., paraformaldehyde or PFA) results in the formation of intra- and inter-molecular covalent crosslinks between biomolecules in the biological sample. In some cases, provision of the fixation reagent, such as formaldehyde, may result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

Other examples of fixation reagents include, for example, organic solvents such as alcohols (e.g., methanol or ethanol), ketones (e.g., acetone), and aldehydes (e.g., paraformaldehyde, formaldehyde (e.g., formalin), or glutaraldehyde). As described herein, cross-linking agents may also be used for fixation including, without limitation, disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a cross-linking agent may be a cleavable cross-linking agent (e.g., thermally cleavable, photocleavable, etc.). In some cases, more than one fixation reagent can be used in combination when preparing a fixed biological sample. Changes to a characteristic or a set of characteristics of a cell or cellular constituents (e.g., incurred upon interaction with one or more fixation agents) may be at least partially reversible (e.g., via rehydration or de-crosslinking). Alternatively, changes to a characteristic or set of characteristics of a cell or cellular constituents (e.g., incurred upon interaction with one or more fixation agents) may be substantially irreversible.

The methods described herein, e.g., for processing fixed samples, may comprise templated ligation. A templated ligation process may comprise contacting a nucleic acid molecule (e.g., an RNA molecule) with a probe molecule. The probe molecule may interact with one or more other probe molecules, for example, comprising a barcode sequence, to generate a probe-barcode complex. An extension reaction may be performed on at least a portion of the probe-barcode complex to generate a nucleic acid product that comprises the barcode sequence and is associated with a sequence of the nucleic acid molecule. Beneficially, the methods described herein may allow barcoding of the nucleic acid molecule without performing reverse transcription on the nucleic acid molecule. The methods herein may comprise ligation-mediated reactions.

A method may comprise contacting a nucleic acid molecule (e.g., an RNA molecule) with a first probe molecule, comprising a first sequence and a second sequence, under conditions sufficient for the first sequence to hybridize to a sequence of the nucleic acid molecule. A second probe molecule comprising a third sequence may hybridize to the second sequence of the first probe molecule. The first probe or the second probe molecule may comprise a barcode sequence (e.g., as described herein). For example, the second probe molecule may be a nucleic acid molecule (e.g., as described herein). In some cases, a splint molecule may be used to link the first and second probe molecules. For example, a fourth sequence of the splint molecule may hybridize to the second sequence of the first probe molecule and a fifth sequence of the splint molecule may hybridize to the third sequence of the second probe molecule.

In another example, a first probe molecule with a first reactive moiety and a second probe molecule with a second reactive moiety may be used. A first sequence of the first probe molecule may hybridize to a first sequence of a nucleic acid molecule and a second sequence of the second probe molecule may hybridize to a second sequence of the nucleic acid molecule. The first and second sequences of the nucleic acid molecule may be adjacent or may be separated by a gap of one or more nucleotides, which gap may optionally be filled (e.g., using a polymerase). The first reactive moiety of the first probe molecule and the second reactive moiety of the second probe molecule may be subjected to conditions sufficient for the first and second reactive moieties to react to provide a linking moiety. For example, a click chemistry reaction involving an alkyne moiety and an azide moiety may be used to provide a triazole linking moiety. In other examples, an iodide moiety may be chemically ligated to a phosphorothioate moiety to form a phosphorothioate bond, an acid may be ligated to an amine to form an amide bond, or a phosphate may be ligated to an amine to form a phosphoramidate bond. In some cases, the probes may be subjected to an enzymatic ligation reaction, using a ligase, e.g., SplintR ligases, T4 ligases, KOD ligases, PBCV1 enzymes, etc. to form a probe-linked nucleic acid molecule. Where the two probes are non-adjacent, gap regions between the probes may be filled prior to ligation. In some instances, ribonucleotides or deoxyribonucleotides are ligated between the first and second probes.

Prior to, in parallel, or subsequent to linking of the first and second probe molecules (e.g., via reaction between their respective reactive moieties), a third probe molecule (e.g., a nucleic acid barcode molecule) may be subjected to conditions sufficient to hybridize to a third sequence of the first probe molecule. The third probe molecule may comprise a barcode sequence. In some cases, a splint molecule may be used to link the first and third probe molecules. In some cases, the first and second probe molecules may be linked to one another such that a loop or "padlock" is formed after hybridization of the first sequence of the first probe molecule to the first sequence of the nucleic acid molecule and the second sequence of the second probe molecule to the second sequence of the nucleic acid molecule. A linkage between the first and second probe molecules may be generated after hybridization of the first and second probe molecules to the nucleic acid molecule, such as via reaction between two reactive moieties to form a linking moiety. Alternatively, the first and second probe molecules may be linked to one another before the first and second probe molecules hybridize to the nucleic acid molecule.

All or a portion of the templated ligation processes described herein may be performed within a partition (e.g., as described herein). Alternatively, one or more such processes may be performed within a bulk solution. For example, one or more probe molecules may be subjected to conditions sufficient to hybridize to a nucleic acid molecule (e.g., a nucleic acid molecule included in an biological particle such as a cell) within a bulk solution. The nucleic acid molecule may be partitioned within various reagents (e.g., as described herein) including a nucleic acid barcode molecule, such as a nucleic acid barcode molecule releasably coupled to a bead (e.g., as described herein). Within the partition, the nucleic acid barcode molecule may hybridize to a sequence of a probe molecule hybridized to the nucleic acid molecule, thereby generated a barcode-linked nucleic acid molecule. Templated ligation processes may permit indirect barcoding of a nucleic acid molecule without the use of reverse transcription. Details of such processes and additional schemes are included in, for example, International Patent Publication No. WO2019/165318, which is herein entirely incorporated by reference for all purposes.

Computer Systems

Figure 14:
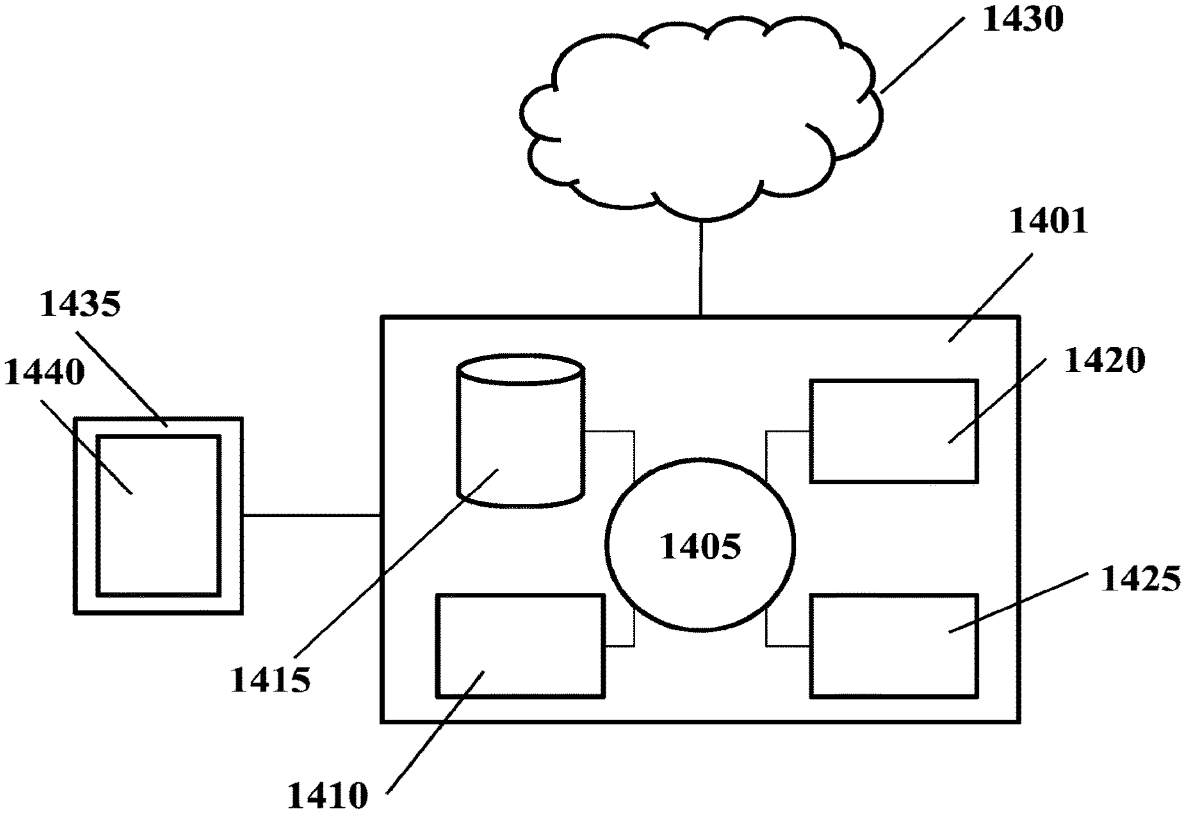
FIG. 14 shows a computer system that is programmed or otherwise configured to implement methods provided herein.

The present disclosure provides computer systems that are programmed to implement methods of the disclosure. FIG. 14 shows a computer system 1401 that is programmed or otherwise configured to: (i) control a microfluidics system (e.g., fluid flow), (ii) detect fluorescent signals, (iii) perform sequencing applications, and/or (iv) generate and maintain a library of sequences from barcoded nucleic acid molecules. The computer system 1401 can regulate various aspects of the present disclosure, such as, for example, e.g., regulating fluid flow rate in one or more channels in a microfluidic structure. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, e.g., perform sequencing, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, an biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Additional embodiments are disclosed in further detail in the following examples, which are provided by way of illustration and are not in any way intended to limit the scope of this disclosure or the claims.

EXAMPLES

Example 1

Figure 7:
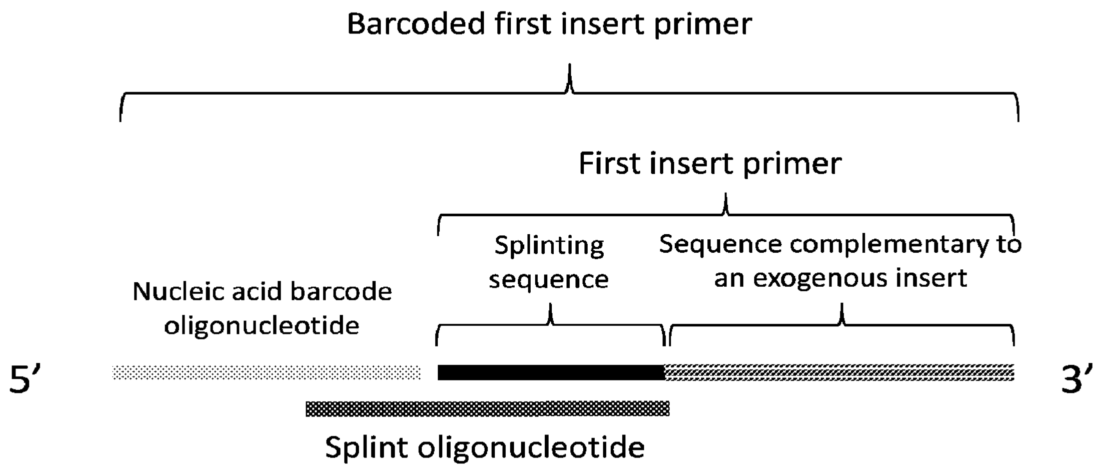
FIG. 7 schematically depicts an example set of components, and how they may be designed, to assemble into a barcoded first insert primer. In the example, a barcoded first insert primer may be assembled from: a nucleic acid barcode oligonucleotide, a first insert primer and a splint oligonucleotide. The nucleic acid barcode molecule of the barcoded first insert primer may include a (i) partition-specific barcode sequence and (ii) capture sequence, where the (ii) capture sequence may hybridize to a sequence of the splint oligonucleotide, e.g. via complementary base pairing. The first insert primer may include a (i) splinting sequence and (ii) sequence complementary to an exogenous insert in a biological particles endogenous nucleic acids wherein the (i) splinting sequence may hybridize to the splint oligonucleotide, e.g., via complementary base pairing. The nucleic acid barcode molecule may be coupled to the first insert primer, following hybridization of the nucleic acid barcode molecule and the first insert primer to the splint oligonucleotide, to form the barcoded first insert primer.

Generation of Barcoded Nucleic Acid Molecules for Exogenous Insert Site Analysis An RT master mix is prepared, e.g., using the Chromium Single Cell 3' Reagent Kit v3 according to manufacturer's instructions. Alternatively, an RT master mix can be prepared using the Chromium Next GEM Single Cell 5' reagent kit according to manufacturer's instructions. To the RT master mix, a splint oligonucleotide and first insert primer (e.g., as depicted in FIG. 7), DNA polymerase, and DNA ligase are added to prepare an Analysis Master Mix. Biological particles, e.g., cells or cell nuclei, are combined with the Analysis Master Mix. Biological particles are combined with the Analysis Master Mix such that an individual biological particle may be partitioned with reagents from the Analysis Master Mix, e.g., the splint oligonucleotide, the first insert primer, DNA polymerase, RT enzyme, DNA ligase, and a plurality of nucleic acid barcode molecules (having a partition-specific barcode sequence and a capture sequence) from the RT Master Mix. Partitioning is carried out, e.g., using a 10× Genomics Chromium microfluidic instrument according to manufacturer's instructions. Alternatively, partitioning can be carried out by portioning the Analysis Master Mix (containing the biological particles) into wells such that an individual well partition comprises an individual biological particle and the reagents from the Analysis Master Mix. The partition is incubated at 25° C. for 10 minutes to couple the first nucleic acid barcode molecule to the first insert primer via splint-mediated ligation, generating a barcoded first insert primer. In embodiments in which the particle's endogenous genomic nucleic acids are single-stranded, the barcoded first insert primer is further hybridized to the first sequence of the exogenous insert of the heterologous nucleic acid molecule during the 25° C. for 10 minute incubation. In embodiments in which the particle's endogenous genomic nucleic acids are double-stranded, the partition is further incubated at about 98° C., and then incubated at about 50° C. to 75° C. to hybridize the barcoded first insert primer to the first sequence of the exogenous insert of the heterologous nucleic acid molecule. A first barcoded nucleic acid molecule is generated by incubation at about 50° C. to about 70° C. In some embodiments in which multiple copies of the first barcoded nucleic acid molecule is generated, multiple cycles of linear PCR (98° C. for 30 seconds; 65° C. for 30 seconds; 72° C. for 1 minute) are performed. Additional barcoded nucleic acid molecules may be generated from, e.g., mRNA analytes, labelling agents comprising reporter oligonucleotides, and CRISPR/gRNA analytes.

Example 2

Processing and Further Analysis of Barcoded Nucleic Acid Molecules

In some embodiments, a double-stranded (ds) derivative of the first barcoded nucleic acid molecule may be prepared from a barcoded nucleic acid molecule. The ds-derivative of the first barcoded nucleic acid molecule may be prepared using the first barcoded nucleic acid molecule and a primer, e.g., random primer, subject to 98° C. for 45 seconds, 65° C. for 30 seconds, and 72° C. for 1 minute. By way of example, the random primer may be of a set of random hexamer primers and the conditions for second strand synthesis may be those of a Second Strand cDNA Synthesis Kit from ThermoFisher Scientific (Catalog numbers A48570 or A48571).

In some embodiments, the ds-derivative of the first barcoded nucleic acid molecule may be digested with a restriction enzyme (RE) having a RE recognition site at the exogenous insert's 5' or 3' end, to yield a fragment of the ds-derivative. RE digestion is performed under appropriate conditions recommended for the RE, e.g., as suggested by its manufacturer. In embodiments in which even further processing steps are desired, the fragment is purified, e.g., via solid phase reversible immobilization (SPRI).

Further processing steps may ligate cDNA primers to the ends of the fragment of the barcoded nucleic acid molecule, e.g., at 25° C. for 10 minutes. The fragment of the barcoded nucleic acid molecules having had cDNA primers ligated thereto is PCR amplified. In some embodiments, adapters, e.g., Illumina adaptors, are added to the amplified products. Sequence insertion site is determined by computationally aligning sequence of the endogenous flanking sequence determined from the barcoded nucleic acid molecule, or any derivative, e.g., as described or as prepared herein, to the biological particle's genomic nucleic acids, or alternatively to a reference genome. Sequence alignment tools include, e.g., Cell Ranger (support.10xgenomics.com/single-cell-gene-expression/software/pipelines/latest/what-is-cell-ranger).

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

The invention claimed is:

1. A method comprising:

a) providing a partition comprising:

(i) a biological particle comprising a heterologous nucleic acid molecule, wherein the heterologous nucleic acid molecule comprises an exogenous insert and endogenous flanking sequences that flank the exogenous insert;

(ii) a plurality of nucleic acid barcode molecules comprising a partition-specific barcode sequence and a capture sequence;

(iii) a first insert primer, comprising from 5' to 3', a splinting sequence and a sequence complementary to a first sequence of the exogenous insert, and (iv) a splint oligonucleotide comprising a sequence complementary to the capture sequence of a first nucleic acid barcode molecule of the plurality of nucleic acid barcode molecules and a sequence complementary to the splinting sequence of the first insert primer;

b) subjecting the partition to conditions sufficient for:

(i) coupling the first nucleic acid barcode molecule to the first insert primer to generate a barcoded first insert primer; and (ii) hybridizing the barcoded first insert primer to the first sequence of the exogenous insert of the heterologous nucleic acid molecule; and c) generating a first barcoded nucleic acid molecule comprising: (i) the partition-specific barcode sequence, or a reverse complement thereof, and (ii) a first endogenous flanking sequence of the endogenous genomic flanking sequences, or a reverse complement thereof.

2. The method of claim 1, wherein the heterologous nucleic acid molecule comprises a double-stranded deoxyribonucleic acid (dsDNA) molecule.

3. The method of claim 1, wherein the exogenous insert comprises a recognition site for a restriction enzyme (RE), wherein the recognition site is at a 5' or 3' end of the exogenous insert.

4. The method of claim 3, wherein the recognition site for the RE differs from a cleavage site for the RE.

5. The method of claim 2, wherein the conditions are further sufficient for denaturing the dsDNA molecule.

6. The method of claim 1, wherein coupling the first nucleic acid barcode molecule to the first insert primer comprises hybridizing: (i) the first nucleic acid barcode molecule to the splint oligonucleotide; and (ii) the first insert primer to the splint oligonucleotide.

7. The method of claim 6, wherein: (i) the sequence complementary to the capture sequence of the first nucleic acid barcode molecule of the splint oligonucleotide hybridizes to the capture sequence of the first nucleic acid barcode molecule; and (ii) the sequence complementary to the splinting sequence of the splint oligonucleotide hybridizes to the splinting sequence of the first insert primer.

8. The method of claim 1, wherein coupling the first nucleic acid barcode molecule to the first insert primer comprises ligating the first nucleic acid barcode molecule to the first insert primer.

9. The method of claim 8, wherein i) the ligating is performed by an enzyme capable of nick repair, and/or ii) the enzyme comprises a ligase or polymerase, and/or iii) the enzyme comprises a DNA polymerase, a reverse transcriptase, or a DNA ligase.

10. The method of claim 1, wherein the barcoded first insert primer hybridized to the first sequence of the exogenous insert of the heterologous nucleic acid molecule is extended into the first endogenous flanking sequence to produce the first barcoded nucleic acid molecule.

11. The method of claim 10, further comprising subjecting the first barcoded nucleic acid molecule to second strand synthesis to yield a double stranded (ds) derivative of the first barcoded nucleic acid molecule.

12. The method of claim 11, further comprising fragmenting the ds derivative of the first barcoded nucleic acid molecule to yield a barcoded fragment thereof.

13. The method of claim 12, wherein the fragmenting is performed by an RE.

14. The method of claim 1, further comprising attaching a first adaptor to the first barcoded nucleic acid molecule, or a derivative, or amplicon, or a barcoded fragment thereof to generate an adapted barcoded product, wherein the first adaptor comprises a reverse primer binding site.

15. The method of claim 14, further comprising amplifying the adapted barcoded product with a first primer that hybridizes to the reverse primer-binding site.

16. The method of claim 15, wherein the plurality of nucleic acid barcode molecules further comprise a forward primer binding site or reverse complement thereof, and wherein the amplifying further comprises amplifying with a second primer that hybridizes to the forward primer binding site.

17. The method of claim 1, wherein the sequence complementary to the first sequence of the exogenous insert is within about 20 to 50 nucleotides of the junction of the exogenous insert and the first endogenous flanking sequence.

18. The method of claim 1, wherein the exogenous insert comprises a recognition site for an RE, wherein the recognition site is: (i) in the sequence complementary to the first sequence of the exogenous insert of the first insert primer, or (ii) between the sequence complementary to the first sequence of the exogenous insert of the first primer and the junction of the exogenous insert and the first endogenous flanking sequence.

19. The method of claim 18, wherein the recognition site for the RE differs from the cleavage site for the RE, and wherein the RE cleavage site is in the first endogenous flanking sequence.

20. The method of claim 1, wherein the exogenous insert encodes a polypeptide or a functional RNA.

21. The method of claim 20, wherein the polypeptide comprises a chimeric antigen receptor, brain-derived neurotrophic factor, hemoglobin (β-chain), adenosine deaminase, p53, dystrophin, alpha-galactosidase A, Factor VIII, Factor IX, lipoprotein lipase or acid alpha-glucosidase.

22. The method of claim 1, further comprising determining expression of an analyte of the biological particle, optionally wherein the analyte is encoded by the exogenous insert.

23. The method of claim 22, wherein the analyte is an mRNA analyte, and expression of the mRNA analyte is determined via generation of a second barcoded nucleic acid molecule, wherein the second barcoded nucleic acid molecule comprises: (i) the partition-specific barcode sequence, or a reverse complement thereof; and (ii) at least a portion of a nucleic acid sequence of the mRNA analyte, or a reverse complement thereof.

24. The method of claim 22, wherein the analyte is a peptide or protein analyte, wherein the expression of the peptide or protein analyte is determined by: further providing in the partition, a labeling agent operatively coupled to a first reporter oligonucleotide, wherein the labeling agent binds the peptide or protein analyte.

25. The method of claim 24, wherein (i) the first reporter oligonucleotide comprises a first reporter barcode sequence and a capture handle sequence, and/or (ii) the plurality of nucleic acid barcode molecules further comprises a further nucleic acid barcode molecule comprising the partition-specific barcode sequence and a further capture sequence, wherein the further capture sequence is configured to couple to the capture handle sequence.

26. The method of claim 25, further comprising generating a further barcoded nucleic acid molecule wherein the further barcoded nucleic acid molecule comprises: (i) the partition-specific barcode sequence, or a reverse complement thereof, and (ii) the first reporter barcode sequence, or a reverse complement thereof, wherein the further barcoded nucleic acid molecule is used to determine expression of the peptide or protein analyte.

27. The method of claim 1, further comprising determining a sequence of the first endogenous flanking sequence of the first barcoded nucleic acid molecule.

28. The method of claim 27, further comprising mapping the exogenous insert as inserted into a location in endogenous sequences of the biological particle based on the determined sequence of the first endogenous flanking sequence, wherein the biological particle is characterized as comprising the exogenous insert at the location in the endogenous sequences.

29. The method of claim 28, further comprising identifying the location as capable of dysregulating expression of one or more endogenous genes of the biological particle, wherein the identifying comprises determining the biological particle is unsuitable for administration as a therapeutic agent to a subject in need thereof.

30. The method of claim 29, wherein the dysregulating comprises: (i) activation of an adjacent endogenous gene, wherein the adjacent endogenous gene comprises an oncogene; (ii) interruption of an endogenous gene; or (iii) silencing an endogenous gene.

31. The method of claim 1, wherein the biological particle is a cell or a nucleus of a cell.

32. The method of claim 31, wherein the cell:

(i) is a T cell, bone marrow progenitor cell, an induced progenitor stem cell, a plasma cell or a retinal cell, and/or (ii) is for administration to a subject, and/or (iii) is autologous or allogeneic to the subject, and/or (iv) has been modified to comprise the exogenous insert by a gene editing protein having sequence-specific integration characteristics.

33. The method of claim 32, wherein the cell is characterized as comprising on-target insertion of the exogenous insert if the first endogenous flanking sequence reflects the sequence-specific integration characteristics of the gene editing protein, and the cell is characterized as comprising off-target insertion of the exogenous insert if the first endogenous flanking sequence does not reflect the sequence-specific integration characteristics of the gene editing protein.

34. The method claim 1, wherein the partition is a well, microwell or droplet.

* * * * *